United States Patent
Kremer et al.

(10) Patent No.: US 10,463,726 B2
(45) Date of Patent: *Nov. 5, 2019

(54) METHOD OF INHIBITING CANCER IN A MAMMAL BY ADMINISTERING AN ANTIBODY TO PTHRP

(71) Applicant: BIOCHROM PHARMA INC., Westmount (CA)

(72) Inventors: Richard Kremer, Westmount (CA); Dao Chao Huang, Montreal (CA)

(73) Assignee: BIOCHROM PHARMA INC., Westmount, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,153

(22) Filed: Aug. 5, 2013

(65) Prior Publication Data

US 2014/0220022 A1    Aug. 7, 2014

Related U.S. Application Data

(63) Continuation of application No. 12/673,877, filed as application No. PCT/CA2008/001478 on Aug. 18, 2008, now Pat. No. 8,501,929, which is a continuation-in-part of application No. 11/889,969, filed on Aug. 17, 2007, now Pat. No. 7,897,139.

(51) Int. Cl.
| | | |
|---|---|---|
| *A61K 39/395* | (2006.01) | |
| *A61K 39/00* | (2006.01) | |
| *C07K 16/26* | (2006.01) | |
| *C07K 16/30* | (2006.01) | |
| *C12N 15/113* | (2010.01) | |
| *A61K 31/713* | (2006.01) | |

(52) U.S. Cl.
CPC ...... *A61K 39/001144* (2018.08); *C07K 16/26* (2013.01); *C07K 16/30* (2013.01); *C07K 16/3015* (2013.01); *C07K 16/3053* (2013.01); *C07K 16/3069* (2013.01); *C12N 15/1136* (2013.01); *A61K 31/713* (2013.01); *A61K 2039/505* (2013.01); *C07K 2317/34* (2013.01); *C07K 2317/73* (2013.01); *C07K 2317/76* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,816,567 A | 3/1989 | Cabilly et al. | |
| 4,965,188 A | 10/1990 | Mullis et al. | |
| 5,614,396 A | 3/1997 | Bradley et al. | |
| 5,660,826 A | 8/1997 | Grunfield et al. | |
| 6,903,194 B1 | 6/2005 | Sato et al. | |
| 2006/0003916 A1* | 1/2006 | Massfelder et al. | 514/2 |

FOREIGN PATENT DOCUMENTS

| | | | |
|---|---|---|---|
| WO | WO97/04312 | * | 2/1997 |
| WO | WO 97/04312 | | 2/1997 |

OTHER PUBLICATIONS

Clark (Protein Engineering of Antibody Molecules for Prophylactic and Therapeutic Applications in Man, 1993, pp. 4-5).*
Terkeltaub et al. (Arthritis and Rheumatism, 41: 2152-2164, 1998).*
Wheeler (Salud p'ublica de M'exico, (Jul.-Aug. 1997) 39 (4) 283-7).*
Efferson et al. Anticancer Research 25: 715-724, 2005.*
Bachmann et al. J. Immunol. 175: 4677-4685, 2005.*
Supplemental European Search Report for EP 08 78 3388.
Saito, H. et al. Humanized monoclonal antibody against parathyroid hormone-related protein suppresses osteolytic bone metastasis of human breast cancer cells derived from MDA-MB-231. Anticancer Research (Nov.-Dec. 2005), vol. 25, No. 6B, pp. 3817-3823, ISSN 0250-7005.
Guise, T.A. et al. Evidence for a causal role of parathyroid hormone-related protein in the pathogenesis of human breast cancer-mediated, osteolysis. Journal of Clinical Investigation (Oct. 1996), vol. 98, No. 7, pp. 1544-1549, ISSN 0021-9738.
Pandian, M.R. et al. Modified immunoradiometric assay of parathyroid hormone-related protein: clinical application in the differential diagnosis of hypercalcemia. Clinical Chemistry (Feb. 1992), vol. 38, No. 2, pp. 282-288, ISSN 0009-9147.
Dittmer, A. et al. Parathyroid hormone-related protein regulates tumor-relevant genes in breast cancer cells. Journal of Biological Chemistry (May 26, 2006), vol. 281, No. 21, pp. 14563-14572, ISSN 0021-9258.
Deftos et al, "Immunoassay for the carboxy terminus of the human-specific isoform of PTHrP: Confirmation of specificity and measurement in biological fluids", Journal of Bone and Mineral Research, vol. 21, No. Suppl. 1, Sep. 2006, p. S446, XP002677559 & 28th Annual Meeting of the American Society for Bone and Mineral Research; Philadelphia, PA, USA; Sep. 15-19, 2006.

(Continued)

*Primary Examiner* — Christine J Saoud
(74) *Attorney, Agent, or Firm* — B. Aaron Schulman, Esq.; Stites & Harbison, PLLC

(57) ABSTRACT

The present disclosure is directed to a method for treating cancer in a mammal by administering a PTHrP inhibitor to the mammal to inhibit expression of the PTHrP1-173 isoform of PTHrP in the mammal wherein the inhibitor is an antibody that specifically binds with an epitope of a C-terminal portion of the human PTHrP1-173 isoform and wherein the C-terminal portion consists of amino acid residues 151 to 169. The method is applicable to several types of cancer including breast, lung, prostate, melanoma and squamous cancer, either alone or in combination with other therapeutic agents.

2 Claims, 24 Drawing Sheets
Specification includes a Sequence Listing.

(56) References Cited

OTHER PUBLICATIONS

Luparello C, et al, "Parathyroid Hormone-Related Peptide and 8701-BC Breast Cancer Cell Growth and Invasion in vitro: Evidence for Growth-Inhibiting and Invasion-Promoting Effects", Molecular and Cellular Endocrinology, Elsevier Ireland Ltd., IE, vol. 111, No. 2, Jun. 1, 1995, pp. 225-232, XP000982374.
Bagi C. Skeletal complications of malignancy—Third North American Symposium. Drugs (2002) 5:553-556.
Birch MA et al. Parathyroid hormone (PTH)/PTH-related protein (PTHrP) receptor expression and mitogenic responses in human breast cancer cell lines. Br J Cancer (1995) 72:90-5.
Bouizar z et al. Polymerase chain reaction analysis of parathyroid hormone-related protein gene expression in breast cancer patients and occurrence of bone metastases. Cancer Res (1993) 53:5076-8.
Bundred et al. Parathyroid hormone related protien and hypercalcemia in breast cancer. Br Med J (1991) 303:1506-1509.
Budayr AA et al. Increased serum levels of a parathyroid hormone-like protein in malignancy-associated hypercalcemia. Ann Intern Med (1989) 111:807-812.
Campos RV et al. Differential expression of RNA transcripts encoding unqiue carboxy-terminal sequences of human parathyroid hormone-related peptide. Mol. Endocrinol. (1994) 8:1656-66.
Carron JA et al. PTHrP and the PTH/PTHrP receptor are co-expressed in human breast and colon tumors. Br J Cancer (1997) 76:1095-8.
CDC Press Release. Latest cancer incidence report shows prostate leading cancer among men, breast cancer leads for women. (2003) http:/www.cdc.gov/cancer.
Christenson LJ et al. Incidence of basal cell and squamous cell carcinomas in a population younger than 40 years. JAMA (2005) 294:681-690.
Deftos LJ. Prostate carcinoma. Production of bioactive factors. Second North American Symposium on Skeletal Complications of Malignancy (1999).
Deftos LJ Cancer (2000) 88, 3002.
Diel IG et al. Reduction in new metastases in breast cancer with adjuvant clodronate treatment. N Engl J Med (1998) 339:357-363.
Fahn HJ et al. The incidence and prognostic significance of humoral hypercalcemia in renal cell carcinoma. J Urol ( 1991) 145:248-250.
Gallwitz WE et al. Guanosine nucleotides inhibit different syndromes of PTHrP excess caused by human cancers in vivo. J. Clin. Invest. (2002) 110:1559-72.
Hall HI et al. Update on the incidence and mortality from melanoma in the United States. J. Am. Acad. Dermatol. (1999) 40:35-42.
Hanahan D et al. The hallmarks of cancer. Cell (2000) 100:57-70.
Harris JR et al. Diseases of the breast. Third edition. Philadelphia PA. LippincoUWilliams & Wilkins(2004) p. 971.
Iwamura M et al. Parathyroid hormone-related protein is an independent prognostic factor for renal cell carcinoma. Cancer (1999) 86:1028-1034.
Kao PC et al. Parathyroid hormone-related peptide in plasma of patients with hypercalcemia and malignancy lesions. Mayo Clin Proc (1990) 65:1399-1407.
Kissin MW et al. Parathyroid hormone related protein in breast cancer of widely varying prognostic. Eur J Surg Oncol (1993) 19:134-142.
Kremer R et al. Parathyroid hormone related peptide in hematologic malignancies. Am J Med (1996) 100:406-411.
El Abdaimi et al Am J Physiol (2000) 279,C1230.
Goding, Monoclonal Antibodies: Principles and Practice, Academic Press, (1986) pp. 59-103.
Grone A et al. Cloning and sequencing of the 3' region of the canine parathyroid hormone-related protein gene and analysis of alternative mRNA splicing in two canine carcinomas. Domest. Anim. Endocrinol. (2002) 22(3): 169-77.
Hardy RR et al. In Handbook of ExperimentalImmmunology (OM Weir Ed) Blackwell Scientific p. 13.1.
Hortobagyi GN et al. Efficacy of pamidronate in reducing skeletal complications in patients with breast cancer and lytic bone metastases. N Eng! .I Med ( 1996) 335:1785-1791.
Insogna KL et al. Native and a synthetic analogue of the malignancy-associated parathyroid hormone-like protein have in vitro transforming growth factor-like properties . .I Clin Invest ( 1989) 83: I 057-1060.
Kohler and Milstein, Nature, 256:495 (1975).
Kumari R et al. Nuclear targeting of a midregion PTHrP fragment is necessary for stimulating growth in breast cancer cells. Int J Cancer (2006) 119:49-59.
Lauth M et al. Non-melanoma skin cancer: pathogenesis and mechanisms. Drug Discovery Today: Disease Mechanisms (2004) 1 :267-72.
Liapis H et al. Expression of parathyroidlike protein in normal, proliferative and neoplastic human breast tissues. Am J Pathol (1993) 143:1169-78.
Rhim JS et ai.Evidence for the multistep value of in vitro human epitheleial cell carcinogenesis. Cancer Res.(1990)50:5653.
Manenti G et al. A cancer modifier role for parathyroid hormone-related protein. Oncogene (2000) 19:5324-28.
Nishihara M et al. Clinicopathological implications of parathyroid hormonerelated protein in human colorectal tumors. J Pathol (1999) 187:217-222.
Percherstorfer M et al. Parathyroid hormone-related protein and life expectancy in hypercalcemic cancer patients. J Clin Endocrinol Metab (1994) 76:1268-1270.
Ralston S et al. Hypercalcaemia and metastatic bone disease: is there a causal link? Lancet (1982) 2:903-905.
Rhim JS et al. Neoplastic transformations of human keratinocytes by polybrene-induced DNA-mediated transfer of an activated oncogene. Oncogene (1989) 4:1403-1409.
Li J et al. Conditional Ablation of Parathyroid Hormone Related Peptide (PTI-IrP) in Mammary Epithelial Cells Inhibits Breast Cancer Progression. Proceedings of the ASBMR 2007.
Linforth R et al. Coexpression of parathyroid hormone related protein and its receptor in early breast cancer predicts poor patient survival. Clin Cancer Res (2002) 8:3172-3177.
Munson and Pollard, Anal. Biochem. 107:220 (1980).
Morrison, Nature 368, 812-13 (1994).
Nishigaki Y et al. Increased serum and urinary levels of a parathyroid hormone-related protein COOH terminus in non-small cell lung cancer patients. Clin Cancer Res (1999) 5:1473-81.
Powell GJ et al. Localization of parathyroid hormone-related protein in breast cancer metastases: increase incidence in bone compared with other sites. Cancer Res (1991) 51 :3059-3061.
Ratcliffe WA et al. Immunoreactivity of plasma parathyrin-related peptide: three region spradioimmunoassay and a two-site immunoradiometric assay compared. Clin Chern (1991) 37: 1781-17.
Richard V et al. Quantitative evaluation of alternative promoter usage and 3' splice variants fer parathyroid hormone-related protein by real-time reverse transcription-PeR. Clin Chem (2003) 49: 1398-1402.
Roodman D. Mechanisms of bone metastasisN.Engi.J.Med. (2004) 350:1655-1664 San Miguel JF et al. Prognostic factors and classification in multiple myeloma. Br J Cancer (1989) 59:113-118.
Sellers RS et al. Alternative splicing of parathyroid hormone-related protein mRNA: expression and stability. J Mol Endocrinol (2004) 33:227-241 Shen X et al. Increased cell survival, migration invasion, and Akt expression overexpressing LoVo cancer cell lines. Regul. Pept. (2007) Jan. 1 0; 17276526.
Shen X et al. PTH-related protein enhances LoVo colon cancer cell proliferation, adh integrin expression. Regul. Pept. (2005) 125:17-27.
Shen X et al. PTH-related protein enhances MCF-7 breast cancer cell adhesion, migr invasion via an intracrine pathway. Exp. Cell Res. (2004) 294:420-33.
Shen X et al. PTH-related protein modulates PC-3 prostate cancer cell adhesion an subunit profile. Mol. Cell Endocrinol. (2003) 199:165-77.
Shields JD et al. Lymphatic density and metastatic spread in human malignant melanoma. British Journal of Cancer (2004) 90:693-700.

(56) References Cited

OTHER PUBLICATIONS

Southby J et al. Immunohistochemical localization of parathyroid hormonerelated protein in human breast cancer. Cancer Res (1990) 50:7710-7716.
Talon I et al. Antitumor effect of parathyroid hormone-related protein neutralizing antibody in human renal cell carcinoma in vitro and in vivo. Carcinogenesis (2006) 27:73-83.
Sato K et al. Treatment of malignancy-associated hypercalcemia and cachexia with humanized antiparathyroid hormone-related protein antibody. Semin Oncol (2003) 30:167-173.
Saskai Cancer Res (1995) 55, 3551.
Terkeltaub R et al. Parathyroid hormone-related proteins is abundant in osteoa11hritic cartilage, and the parathyroid hormone-related protei 1-173 isoform is selectively induced by transforming growth factor beta in articular chondrocytes and suppresses generation of extracellular inorganic pyrophosphate. Arthritis Rheum. ( 1998) 41 :2152-64.
Truong UN et al. Parathyroid hormone related peptide (PTHrP) is a prognostic indicator in hypercalcemic cancer patients with skeletal or extra skeletal metastasis. J Bone Miner Res (1999) 14:S 189.
Yoshida A et al. Significance of the parathyroid hormone-related protein expression in breast carcinoma. Breast Cancer (2000) 7:215-20.
Won C et al. Hypercalcemia in head and neck carcinoma. Incidence and prognosis. Cancer (1983) 52:2261-2263.

\* cited by examiner

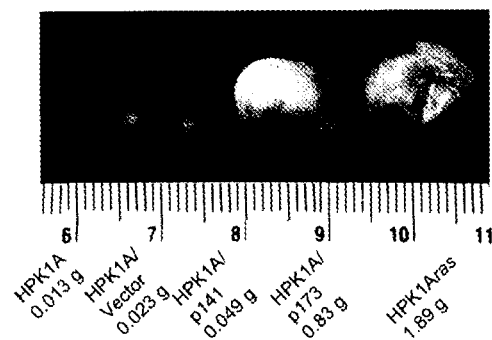
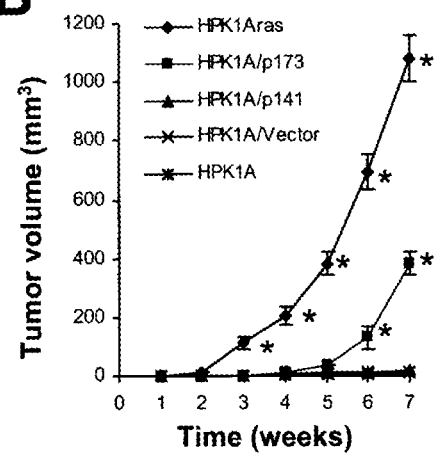
FIGURE 2

Figure 5. Characterization of monoclonal antibodies.

| PTHrP antigen | mAb clone | Isotype subclass | Application | | |
|---|---|---|---|---|---|
| | | | ELISA | IHC | WB |
| 1-33 | 158 | IgG3 | + | + | + |
| | M45 | IgM*k* | + | n.d | n.d |
| 140-173 | 104 | IgG2b*k* | + | + | + |
| | M18 | IgM*k* | + | n.d | n.d |
| 151-169 | 6 | IgG1*k* | + | + | n.d |

ELISA: enzyme-linked immunosorbent assays
IHC: immunohistochemistry
WB: western blot
n.d: not determined

Figure 9.

| Metastatic site | Lung | Liver | Kidney | Pancreas | Heart muscle | Intra-ventricular | Lymph node | Bone |
|---|---|---|---|---|---|---|---|---|
| WT (+/+) A375 | 12/14 | 12/14 | 7/14 | 6/14 | 7/14 | 0/14 | 10/14 | 12/14 |
| DKO (-/-) A375 | 6/14 | 5/14 | 0/14 | 0/14 | 0/14 | 5/14 | 5/14 | 10/14 |

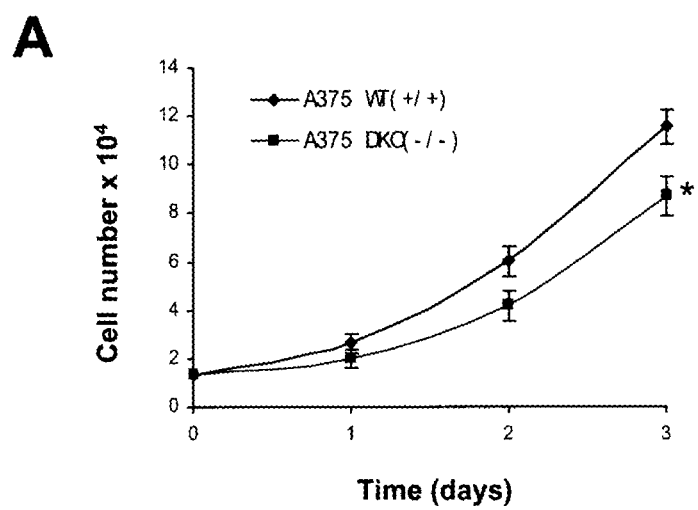
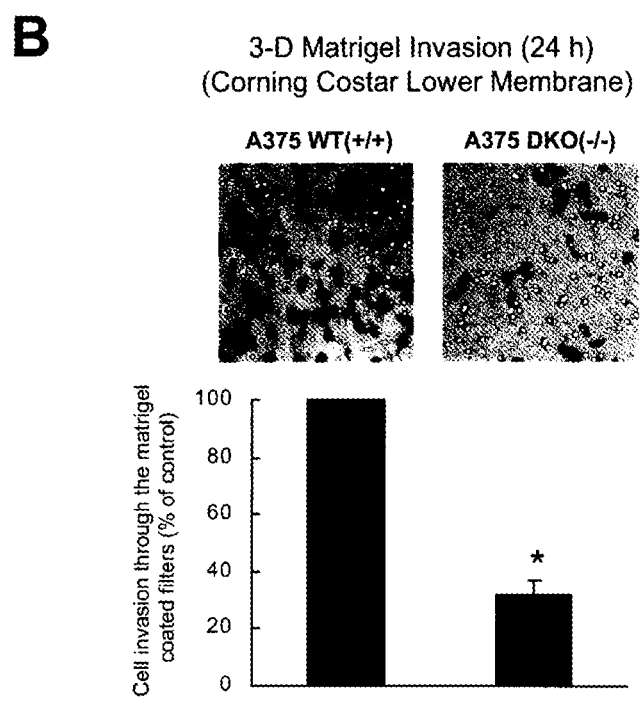
FIGURE 10

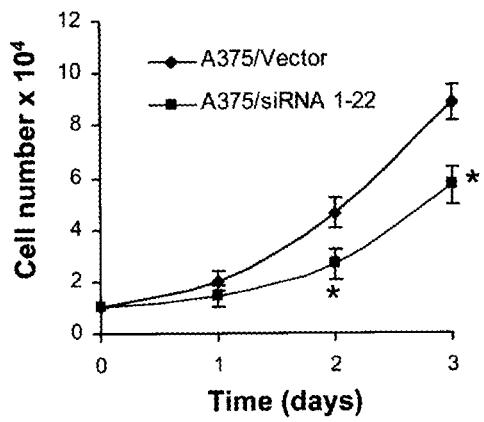
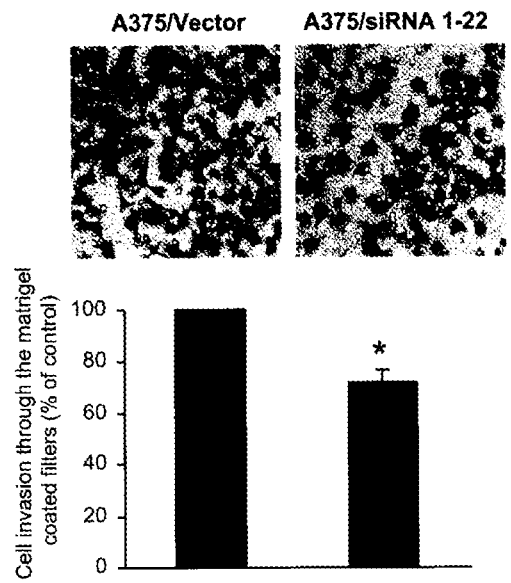
FIGURE 13

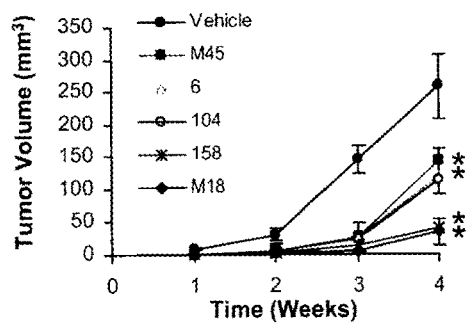
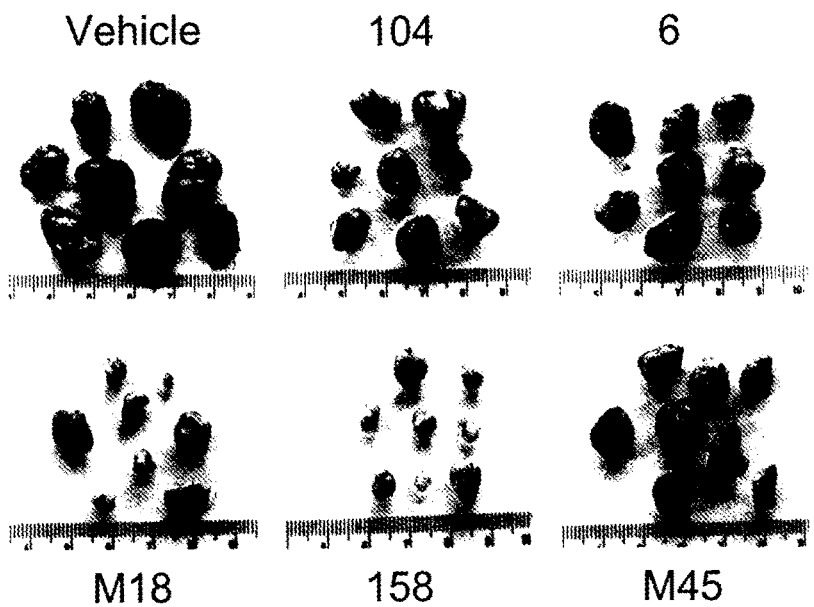
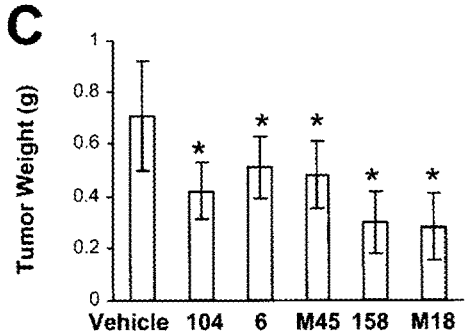
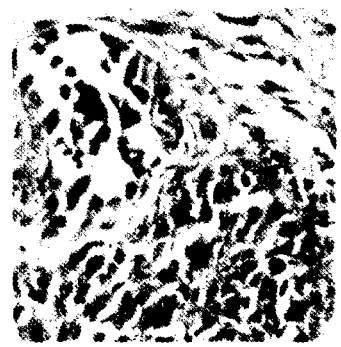
FIGURE 14

Figure 16. Recurrence of metastatic spread 4 months (at 8 months of age) following discontinuation of monoclonal antibody therapy in nu/nu mice transplanted with A375 cells into the left ventricle

|  | Number of animals Alive at 7- 8 months) | Autopsy findings (metastasis) |
|---|---|---|
| M45 (PTHrP 1-33 Specific mAb) | 4/14 (28%) | 2/4* (50%) |
| M18 (PTHrP 140-173 Specific mAb) | 4/15 (27%) | 0/4° (0%) |

*, 1 animal with renal tumor, 1 animal with liver tumor;

°, No evidence of metastatic spread in all organs examined.

METHOD OF INHIBITING CANCER IN A MAMMAL BY ADMINISTERING AN ANTIBODY TO PTHRP

CROSS-REFERENCE TO RELATED APPLICATIONS

This is a Continuation of U.S. application Ser. No. 12/673,877, filed Mar. 14, 2011, and issued as U.S. Pat. No. 8,501,929 on Aug. 6, 2013; which application is a § 371 National Stage of International Application No. PCT/CA2008/001478 filed Aug. 18, 2008; which is a continuation-in-part of application Ser. No. 11/889,969, filed Aug. 17, 2007 which issued as U.S. Pat. No. 7,897,139 on Mar. 1, 2011 (all hereby incorporated by reference).

FIELD OF THE INVENTION

The present invention relates to Parathyroid Hormone-Related Protein (PTHrP), isoforms thereof and antagonists thereto in the diagnosis and treatment of disease, particularly cancer.

BACKGROUND OF THE INVENTION

Tumors are known to arise from normal cells through a series of stepwise transformations. Activation of signaling molecules and in particular growth factor related pathways could lead to malignant transformation of normal cells. Cancer mortality can be linked to the ability of tumors to undergo metastatic spread. The spread of tumors from the original site and the ability thereof to home in to specific tissues likely involves multiple steps as tumors are progressing from a non-invasive to an invasive state.

PTHrP was initially discovered as a mediator of malignancy associated hypercalcemia due to PTHrP's strong sequence homology at its amino or N-terminus with parathyroid hormone (PTH) at PTH's amino terminal end. The majority of patients with advanced cancer and hypercalcemia have been shown to have elevated circulating levels of PTHrP with or without associated osteolytic skeletal metastasis.

PTHrP is associated with the great majority of malignancies in the context of hypercalcemia including breast, colon, skin, renal and lung as well as hematological malignancies such as lymphomas, leukemias and multiple myelomas. Even more significant, in the absence of hypercalcemia and of elevation of circulating PTHrP levels, the expression of PTHrP in these tumor tissues has been shown to be elevated. Furthermore, several studies indicate that PTHrP may be a prognostic indicator in cancer patients and correlates with the metastatic process in several types of cancer including breast, prostate and colon cancer. Several studies suggest that PTHrP stimulates invasion in vitro and bone metastasis in vivo. The mechanism underlying PTHrP stimulation of bone metastasis is believed to be indirect by activating osteoclastic bone resorption and the release of local growth factors within the bone microenvironment that in turn stimulate growth of tumor cells within bone. The main target for treating bone metastasis in patients currently uses agents that reduce osteoclastic activity such as the class of agents known as bisphosphonates. PTHrP inhibition has therefore been identified as a potential target to inhibit osteoclastic activity within bone by reducing PTHrP production of tumor cells within bone. Monoclonal antibodies ("mAbs") directed at the N-terminus of PTHrP have been used successfully in reducing osteolytic bone metastasis in nude mice transplanted with the human cell line MDAMB231. Humanized monoclonal antibodies directed at the N-terminal end of PTHrP have been generated and shown to be effective in nude mice models of hypercalcemia and bone metastasis. Clinical trials in patients with osteolytic bone metastasis with humanized monoclonal PTHrP antibodies directed to the N-terminus are currently underway.

In addition to its indirect effect on the bone metastatic process, several studies suggest that PTHrP may directly affect the growth and invasive abilities of tumor cells. Most of these studies were conducted in vitro and tend to indicate that PTHrP stimulates invasion and migration in different cell lines including breast, prostate and melanoma. In vivo data aside from studies on bone metastasis are very limited. One study indicate that PTHrP may be responsible for the growth of renal cancers and that growth and maybe metastasis is reduced by the administration of an antibody directed at the N-terminal end of PTHrP in nude mice transplanted with a human renal cancer cell line.

Because the PTH-like activity of PTHrP appears to lie within the N-terminal portion of the molecule, studies have used N-terminal fragments for in vitro and in vivo studies, particularly for studies of the PTH/PTHrP receptor Type-1 which can be activated by both PTH and PTHrP 1-34. This receptor has 7 transmembrane domains linked to G-Proteins and belongs to G-Protein coupled receptors (GPCRs). Ligand binding results in activation of both adenylate cyclase (cAMP pathway) and phospholipase C (PLC). Another PTH receptor (Type-2) has been cloned, is activated by a different ligand called TIP and is found mainly in the central nervous system whereas PTHrP Type-1 Receptor is ubiquitously expressed in most tissues. Furthermore, both the PTHrP Type-1 receptor and PTHrP are expressed simultaneously in the majority of breast carcinomas and this co-expression predicts poor survival.

The gene structure of human PTHrP is far more complex than PTH spanning over twenty (20) kilobases (kb) of genomic DNA and alternative mRNA splicing thereof gives rise to three isoforms of one-hundred and thirty-nine amino acids (139), one-hundred and forty-one amino acids (141) and one-hundred and seventy-three (173) amino acids. There is strong sequence homology between species but alternate splicing has not been reported in the lower species except for the canine gene. The mouse, rat, rabbit, bovine and chicken genes may only give rise to the isoform comprised of one-hundred and thirty-nine (139) amino acids. There is considerable divergence among species in the C-terminal end of PTHrP beyond amino acid 111. The long form, PTHrP1-173 may be unique to humans but its function is currently unknown although it has been suggested to play a role in cartilage growth. Antibodies directed to the N-terminus of PTHrP typically recognize all isoforms of PTHrP.

Despite the many years of research in this area, however, it remains to find the role of PTHrP and particularly its isoforms in diagnosis and treatment of disease, particularly cancer, tumor metastasis, osteolytic bone metastasis and hypercalcemia.

SUMMARY OF THE INVENTION

An embodiment of the present invention is the use of PTHrP or its isoforms as a diagnostic agent and treatment for disease, including several types of cancer.

A further embodiment of the present invention is inhibition of PTHrP or its isoforms, preferably isoform PTHrP 1-173, to treat tumor growth and metastatic spread thereof in several types of cancer.

Another embodiment of the present invention is directed to antibodies directed against PTHrP, preferably the C-terminal portion of PTHrP and more preferably amino acid residues 140 to 173 or amino acid residues 151 to 169 of PTHrP1-173. A further aspect of the present invention is antibodies directed against the C-terminal portion of PTHrP, preferably the amino acid residues 140 to 173, used in combination with antibodies directed to the N-terminus of PHTrP to develop specific immunoassays for detection of specific isoforms of PTHrP, including, but not limited to, sandwich assays such as IRMA, ELISA and chemiluminescent assays. The immunoassays may be used to specifically detect the isoform PTHrP 1-173 in pre and post therapy. The immunoassays may also be used as prognostic indicators in a variety of cancers expressing the PTHrP 1-173 isoform.

Another embodiment of the present invention is determining which tumors express isoform PTHrP 1-173 in order to enhance treatment.

Another embodiment of the present invention relates to the transformation of immortalized cells into tumorigenic cells using the PTHrP isoform 1-173, the effect of PTHrP on cell growth and metastasis, the reduction of tumor growth and metastasis following blockade/disruption of PTHrP production, the effect of monoclonal antibodies against the C-terminal domain of PTHrP1-173 isoform, preferably directed against amino acid residues 140-173 and methods and imaging technology to detect the specific PTHrP 1-173 isoform.

Another embodiment of the present invention is a method of inhibiting the growth, metastatsis and invasion of tumor cells by administering to a patient a therapeutically effective amount (e.g. an amount that eliminates or reduces the patient's tumor burden) of antibodies of the present invention, preferably humanized monoclonal antibodies that specifically bind to the PTHrP1-173 isoform. The mAbs of the present invention, preferably humanized mAbs, can be administered parenterally in a suitable vehicle either subcutaneously, intramuscularly, intravenously or within the tumor itself.

Another embodiment of the present invention is directed to siRNA and siRNA constructs for use in modulating the level of PTHrP, preferably the PTHrP1-173 isoform, activity in a cell. Another embodiment is directed to siRNA and siRNA constructs to modulate, knock out or reduce (e.g. knock down) expression of PTHrP or its various isoforms of PTHrP, preferably the PTHrP isoform 1-173.

A further embodiment of the present invention is directed to methods of antagonizing PTHrP 1-173 including antibodies, preferably monoclonal antibodies, gene therapy, preferably using knock out or knock down techniques or siRNA, more preferably siRNA, and specific antagonists against PTHrP 1-173 or its receptor and/or signaling molecules, preferably peptide fragments of PTHrP, more preferably peptide fragments derived from the C-terminus of PTHrP1-173.

A further embodiment of the present invention is directed to immunochemical derivatives of the mAbs of the present invention including, but not limited to (a) labeled (e.g. radiolabeled, enzyme-labeled or fluorochrome labelled) monoclonal antibodies of the present invention, preferably humanized mAbs, for diagnosing or detecting tumors and tumor spread (e.g. metastasis) using known imaging technologies; and (b) immunotoxin conjugates of the mAbs of the present invention, preferably humanized mAbs, where the mAbs of the present invention are conjugated to known cytotoxic, radioactive or radiolabelled moieties (e.g. radioimmunotherapy) for therapeutic ablation.

Further embodiments of the present invention are directed to an isolated antibody that specifically binds with the C-terminus of the PTHrP1-173 isoform, wherein antibody can be linked to a diagnostic or therapeutic agent.

A further embodiment of the present invention is directed to methods for producing an antibody, comprising: a) administering a polypeptide antigen to a host animal, preferably a mouse, to induce antibody production against the polypeptide antigen in the host animal, the polypeptide selected from PTHrP, preferably the C-terminal portion of PTHrP and more preferably amino acid residues 140 to 173 or amino acid residues 151 to 169 of PTHrP1-173; b) monitoring antibody titer produced by the administration of the peptide antigen in the host animal; c) extracting antisera produced in the host animal; and d) isolating and selecting at least one antibody from the antisera.

A further embodiment of the present invention is directed to methods for treating growth, metastasis or invasion of cancer cells, the method comprising administering to a subject in need of such treatment an effective amount of an isolated antibody that specifically binds PTHrP, preferably the C-terminal portion of PTHrP and more preferably amino acid residues 140 to 173 or amino acid residues 151 to 169 of PTHrP1-173.

A further aspect of the present invention is directed to a method for diagnosing disease activity or metastatic spread of cancer cells, preferably prior to the development of hypercalcemia, the method comprising administering to a subject in need of such treatment an effective amount of an isolated antibody that specifically binds with PTHrP, preferably the C-terminal portion of PTHrP and more preferably amino acid residues 140 to 173 or amino acid residues 151 to 169 of PTHrP1-173. In a preferred embodiment, the cancer cells can be selected from the group consisting of breast, lung, prostate, melanoma and squamous cancer cells.

A further aspect of the present invention is directed to a method of modulating expression of PTHrP, preferably PTHrP1-173, by administration of an siRNA that hybridizes to a nucleic acid molecule encoding human PTHrP, preferably PTHrP1-173.

A further aspect of the present invention is directed to a siRNA composition comprising a siRNA molecule that hybridizes to a nucleic acid molecule encoding human PTHrP, preferably PTHrP1-173, more preferably amino acid residues 140-146 of the C-terminal region of PTHrP.

A further aspect of the present invention is directed to a method of inhibiting expression of PTHrP in a patient comprising administering to the patient siRNA molecules that hybridizes to a nucleic acid molecule encoding human PTHrP in the patient thereby effecting the inhibition.

A further aspect of the present invention is directed to a hybridoma deposited with the IDAC under Accession Number 150807-02.

A further aspect of the present invention is directed to a hybridoma deposited with the IDAC under Accession Number 150807-01.

A further aspect of the present invention is directed to a hybridoma deposited with the IDAC under Accession Number 150807-03.

BRIEF DESCRIPTION OF THE DRAWINGS

The foregoing and other objects, features and advantages of the present invention should become apparent from the following description when taken in conjunction with the accompanying drawings. The patent or patent application file contains at least one drawing executed in colour. Copies of this patent or patent application publication with colour drawing(s) may be provided by the office upon request and payment of the necessary fee.

Table 1 shows the production of PTHrP in different cell lines of the present invention prior to and following transfection of the expression vectors expressing specific PTHrP isoforms.

FIGS. 2(A) & (B) show excised subcutaneous tumors in nude mice transplanted with the PTHrP overexpressing cell line HPK1A/p173 and HPK1A/p141 (A) and tumor growth velocity in nude mice transplanted with the cell lines HPK1A/p173 and HPK1A/p141 (B).

FIG. 5 is a table showing the characterization of PTHrP antibodies subclasses of the present invention against the different isoforms;

FIG. 9 is a table showing the inhibition of metastasis at different sites in nude mice transplanted with A375 cells in which PTHrP has been ablated (DKO−/−) as compared to animals transplanted with wild type cells (WT+/+). +/+). FIG. 9 shows metastasis to various organs of melanoma WT A375 (+/+) and knockout (DKO−/−) transplanted into nu/nu mice. Cells (1×105) were inoculated into the left cardiac ventricle. At sacrifice, each organ was examined macroscopically and microscopically for metastatic involvement. The number of animals positively identified with metastasis in different organs over the total number of animals is shown. There were 14 mice per group.

FIGS. 10(A) and (B) show the results of PTHrP inhibition of all three isoforms by homologous recombination in double knock out mice (DKO−/−) in A375 human melanoma cells on cell growth and invasion in vitro. The asterisk (*) indicates a statistically significant difference between A375 DKO(−/−) and A375 WT(+/+) cells (p≤0.01).

FIGS. 13(A) and (B) show the effect of the neutralizing activity of siRNA against all PTHrP isoforms on cell growth and invasion of A375 cells. The asterisk (*) indicates a statistically significant difference between A375 cells treated with control siRNA (Vector) and A375 cells treated with siRNA1-22 (p≤0.01).

FIGS. 14(A) to (D) show the effect of monoclonal antibodies of the present invention in vivo on tumor growth in nude mice transplanted with A375 cells subcutaneously. (A) tumor growth, (B) photographs of excised tumors, (C) tumor weight at sacrifice and (D) H&E of an excised tumor. The asterisk (*) indicates a statistically significant difference between tumor size or weight of animals treated with vehicle control and animals treated with the various mAbs (p≤0.01).

FIG. 16 is a table showing the recurrence of metastatic spread after discontinuation of monoclonal antibodies in animals injected with A375 cells into the left cardiac ventricle.

DETAILED DESCRIPTION OF THE INVENTION

Figure 1:
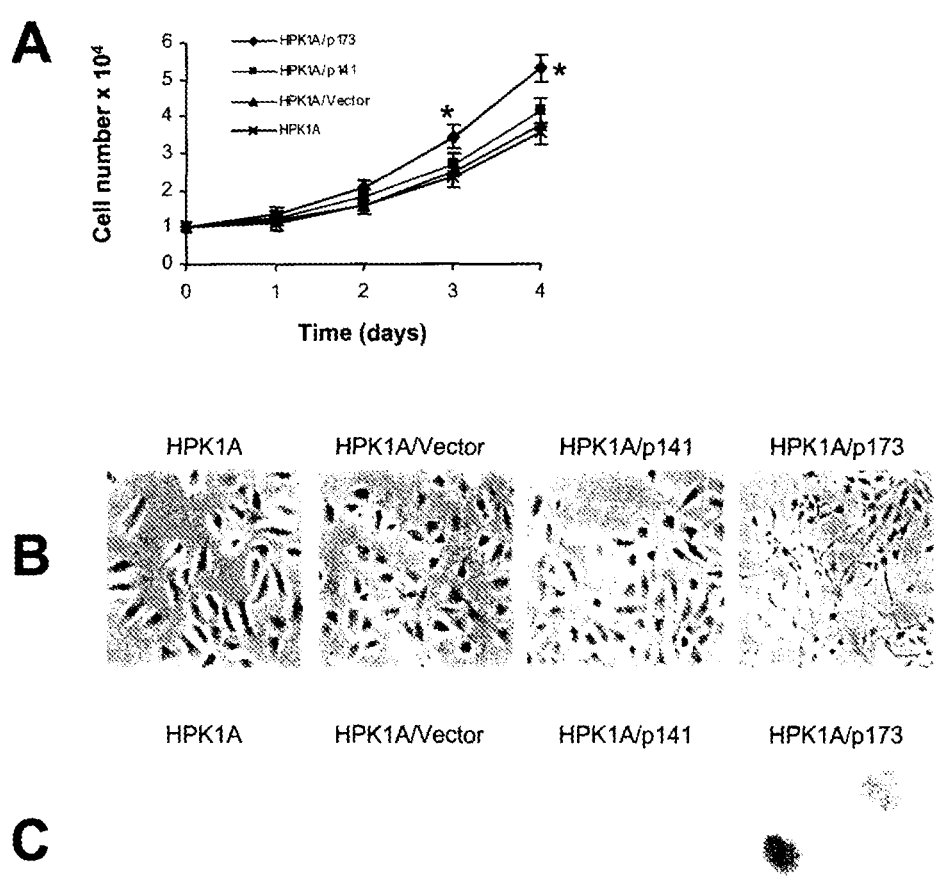
FIGS. 1(A) to (C) show the effect of the overexpression of PTHrP isoforms in HPK1A cells on cell morphology (B), cell growth (A) and on growth in soft agar (C). The asterisk (*) indicates a statistically significant difference between the HPK1A/p173 cell line and either HPK1A/p141, HPK1A/Vector or wild type HPK1A (p≤0.01).

In this disclosure, a number of terms and abbreviations are used. The following definitions of such terms and abbreviations are provided.

As used herein, a person skilled in the relevant art can generally understand the term "parathyroid hormone-related protein" or its abbreviation "PTHrP" refers to the protein PTHrP or one of its isoforms, individually or collectively or when used in reference to a nucleic acid, the nucleic acid encoding PTHrP. In reference to one of the various isoforms according to the present invention, the isoform can be referred to by the abbreviation PTHrP followed by the number of amino acid residues provided in that isoform. For example, the isoform comprising 173 amino acid residues can be referred to as PTHrP1-173.

As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

As used herein, a person skilled in the relevant art may generally understand the term "treatment" to generally refer to an approach for obtaining beneficial or desired results. Beneficial or desired results can include, but are not limited to, alleviation or amelioration of one or more symptoms or conditions, diminishment of the extent of a disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a person skilled in the relevant art may generally understand the term "therapeutically effective amount" to be an amount sufficient to effect treatment when administered to a subject in need of treatment. In the case of the embodiments of the present invention, a therapeutically effective amount can include, but is not limited to, an amount that eliminates or reduces the effects of the disease, such as for example, the tumor burden, in a subject.

As used herein, a person skilled in the relevant art may generally understand the term "amino acid sequence" to refer to an amino acid sequence of a naturally or non-naturally occurring protein molecule, "amino acid sequence" and like terms, such as "polypeptide" or "protein", are not meant to limit the amino acid sequence to the complete, native amino acid sequence associated with the recited protein molecule. Amino acid sequences can be referred to as having an amino (N) terminus and a carboxyl (C) terminus. Individual amino acids in a peptide or polypeptide can be referred to as "residues" and such residues are numbered sequentially beginning from the N-terminus and increasing towards the C-terminus. The amino acids located generally proximal to the N-terminus are generally referred to as the N-terminal amino acids while those located generally proximal to the C-terminus are referred to as the C-terminus amino acids. It will be understood by a person skilled in the relevant art that the reference to amino acid residues as either N terminus or C-terminus amino acid residues may vary depending on the protein. It will be understood by a person skilled in the relevant art generally, the N-terminus of PTHrP extends generally from amino acid residues 1 to 36, the middle or mid portion extends generally from amino acid residue 37 to 106 and the C-terminus generally starts at amino acid residue 107 until the end of the amino acid chain.

As used herein, a person skilled in the relevant art may generally understand the terms "nucleic acid molecule encoding", "DNA sequence encoding," "RNA sequence encoding," "mRNA sequence encoding," "an oligonucleotide having a nucleotide sequence encoding a gene" "polynucleotide having a nucleotide sequence encoding a gene," "DNA encoding", "RNA encoding" and similar terminology to generally refer to the order or sequence of nucleotides along a single or double strand of nucleic acid comprising the coding region of a gene or, in other words, the nucleic acid sequence that encodes a gene product. The order of these nucleotides determines the order of amino acids along the polypeptide chain. The coding region may be present in a cDNA, genomic DNA, or RNA form. The oligonucleotide or polynucleotide may be single-stranded (e.g. the sense strand) or double-stranded (e.g. antisense and sense strands). Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in expression vectors may contain endogenous enhancers/promoters, splice junctions, intervening sequences, polyadenylation signals, etc. or a combination of both endogenous and exogenous control elements.

A person skilled in the relevant art will understand that nucleic acid molecules are said to have "5' ends" and "3' ends" because mononucleotides are linked via a phosphodiester linkage to make oligonucleotides or polynucleotides in a manner such that the 5' phosphate of one mononucleotide pentose ring is attached to the 3' oxygen of its neighbor in one direction. Therefore, an end of an oligonucleotides or polynucleotide, referred to as the "5' end" if its 5' phosphate is not linked to the 3' oxygen of a preceding mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular nucleic acid molecule, discrete elements are referred to as being "upstream" or 5' of the "downstream" or 3' elements. As a DNA molecule is typically provided in a double helix, the DNA molecule is said to have a "sense" strand and an "antisense" strand. The sense strand and the antisense strand are said to be reverse complementary in that the 3' end of the sense strand may anneal to the 5' end of the antisense strand and the 5' end of the antisense strand may anneal to the 3' end of the sense strand. The "sense" strand of the DNA molecule is typically copied into a messenger RNA (mRNA) during transcription. The mRNA made during transcription thus has the same sequence as the sense strand through transcription of the antisense strand so that the eventual protein may be based on the sense version of the DNA molecule. The term "antisense strand" is used in reference to a nucleic acid strand that is complementary to the "sense" strand. The designation (−) (i.e. "negative") is sometimes used in reference to the antisense strand, with the designation (+) (i.e. "positive") is sometimes used in reference to the sense.

As used herein, a person skilled in the relevant art may generally understand that the term "antisense" can also be used in reference to RNA sequences that are complementary to a specific RNA sequence (e.g. mRNA). Antisense RNA may be produced by any method, including synthesis by splicing the gene(s) of interest in a reverse orientation to a viral promoter that permits the synthesis of an RNA molecule that is a copy of the antisense strand (e.g. based on transcription of the sense or coding strand). Once introduced, the transcribed strand combines with natural mRNA produced to form RNA/RNA double stranded molecules. These RNA/RNA double stranded molecules then can interfere with either the further transcription of the mRNA or its translation.

As used herein, a person skilled in the relevant art may generally understand that the terms "complementary" or "complementarity" are used in reference to polynucleotides (i.e. a sequence of nucleotides) related by the base-pairing rules. For example, for the sequence 5'-"A-G-T-3'," is complementary to the sequence 3'-"T-C-A-S'." Complementarity may be "partial," in which only some of the nucleic acids' bases are matched according to the well known base pairing rules, or there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "homology" refers to a degree of complementarity. There may be partial homology or complete homology (i.e. identity). Homologous nucleotide sequences also include, but are not limited to, naturally occurring allelic variations and mutations of the nucleotide sequences set forth herein. As applied to polypeptides, the term "substantial homology" as used herein means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g. 99 percent sequence identity). Amino acid sequences may differ by conservative amino acid substitutions. A person skilled in the relevant art will understand the term "conservative amino acid substitutions" to refer to the general interchangeability of residues having chemically similar side chains. For example, a group of amino acids having aliphatic side chains may comprise glycine, alanine, valine, leucine, and isoleucine; a group of amino acids having aliphatic-hydroxyl side chains may comprise serine and threonine; a group of amino acids having amide-containing side chains may comprise asparagine and glutamine; a group of amino acids having aromatic side chains may comprise phenylalanine, tyrosine, and tryptophan; a group of amino acids having basic side chains may comprise lysine, arginine, and histidine; and a group of amino acids having sulfur-containing side chains may comprise cysteine and methionine.

A person skilled in the relevant art may generally understand that a gene may produce multiple RNA species that are generated by differential or alternatively splicing of the primary RNA transcript. When these multiple RNA species are transcribed into polypeptides, the transcribed polypeptides are referred to as "isoforms". cDNAs that are splice variants of the same gene may contain regions of sequence homology (representing the presence of the same exon or portion of the same exon on both cDNAs) and/or may contain regions of non-homology. If the two cDNAs contain regions of sequence homology, such cDNAs may both hybridize to a probe derived from the entire gene or portions of the gene containing sequences found on both cDNAs. Isoforms can be expressed in different tissues of the same organism as a result of, for example, alternative splicing of RNA. Alternatively, isoforms can be encoded by different genes.

As used herein, the term "hybridization" or "hybridize" is used in reference to the pairing of complementary nucleic acids. Hybridization and the strength of hybridization (i.e. the strength of the association between the nucleic acids) is impacted by such factors as the degree of complementary between the nucleic acids, stringency of the conditions involved, the $T_m$ of the formed hybrid, and the G:C ratio within the nucleic acids. One skilled in the relevant understands that stringency conditions may be altered to impact hybridization (see, for example, Anderson and Young, Quantitative Filter Hybridization, in Nucleic Acid Hybridization [1985] and Sambrook et al. Molecular Cloning: A Laboratory Manual, Cold Spring Harbor Press, NY [1989], which are hereby incorporated by reference).

The term "fragment" as used herein in reference to single chain amino acid sequences refers to a polypeptide that may have an amino (N) terminus portion and/or carboxy (C) terminus portion deleted as compared to the native protein, but wherein the remaining amino acid sequence of the fragment is identical to the amino acid sequence of the native protein. It will be understood by a person skilled in the relevant art that the term "fragment" may also refer to a portion of a multi-chain protein molecule (e.g. antibody fragment)

The term "naturally-occurring" or "native" as used herein as applied to an object refers to the fact that an object can be found in nature. For example, a polypeptide or polynucleotide sequence that is present in an organism (including viruses) that can be isolated from a source in nature and which has not been modified is naturally-occurring.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e. in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers may depend on many factors, including temperature, source of primer and the use of the method. In an amplification reaction, the primer that primes at the 5' end of the nucleotide sequence is referred to as the forward primer, while the primer that primes from the 3' end is generally referred to as the reverse primer.

As used herein, the term "probe" can refer to an oligonucleotide (i.e. a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It may also be understood by a person skilled in the relevant art that a "probe" used in the present invention may also be a protein molecule (e.g. antibody). It may be further understood that the probe may be labeled with any "reporter molecule" so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label. The term "tagged" as used herein (e.g. where a molecule has been "tagged") may also be understood by a person skilled in the relevant art to be linked to a reporter molecule.

As used herein, the term "target," refers to a structure, such as, for example, a nucleic acid or protein molecule, to be identified, detected, characterized or amplified. Thus, the "target" is sought to be sorted out from other structures.

As used herein, the term "polymerase chain reaction" ("PCR") refers to the method first described in U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." Reverse transcription polymerase chain reaction (RT-PCR) as use herein refers to amplifying a defined piece of a ribonucleic acid (RNA) as its DNA complement using reverse transcriptase prior to undergoing a PCR reaction. (e.g. In particular, the amplified segments created by the PCR process itself are, themselves, efficient templates for subsequent PCR amplifications.

As used herein, the terms "PCR product," "PCR fragment," "PCR amplified" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, a person skilled in the relevant art will understand the term "small interfering RNA" or "siRNA" as a class of RNA molecules involved in the RNA interference (RNAi) pathway where the siRNA interferes with the expression of a specific gene products. Synthetic double stranded oligonucleotides can be cloned into siRNA vectors in a manner well known in the art. The siRNA vectors are then transfected into a host to express the siRNA product.

The term "isolated" when used in relation to a nucleic acid or peptide, as in "an isolated oligonucleotide", "isolated polynucleotide" or "isolated polypeptide", refers to a nucleic acid or amino acid sequence that is identified and separated from at least one contaminant with which it is ordinarily associated in its natural source. Isolated compounds are present in a form or setting that is different from that in which it is found nature. In contrast, non-isolated compounds, such as nucleic acids or amino acid sequences, are found in the state they exist in nature. For example, a given DNA sequence (e.g. a gene) is found on the host cell chromosome in proximity to neighboring genes; RNA sequences, such as a specific mRNA sequence encoding a specific protein, are found in the cell as a mixture with numerous other mRNAs that encode a multitude of proteins.

As used herein, the term "portion" when in reference to a nucleotide sequence or a amino acid sequence refers to fragments of that sequence.

As used herein, the term "coding region" when used in reference to gene sequences refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e. TAA, TAG, TGA).

As used herein, the term "purified" or "to purify" refers to the removal of contaminants from a sample. For example, anti-PTHrP antibodies are purified by removal of contaminating non-immunoglobulin proteins; they are also purified by the removal of immunoglobulin that does not bind PTHrP. The removal of non-immunoglobulin proteins and/or the removal of immunoglobulins that do not bind PTHrP results in an increase in the percent of PTHrP-reactive immunoglobulins in the sample.

The term "recombinant protein" or "recombinant polypeptide" as used herein refers to a protein molecule that is expressed from a recombinant DNA molecule.

Numerous techniques that are well known in the art are used to detect antibody binding in association with the present invention. These techniques include, but not limited to RIA (radioimmunoassays), ELISA (enzyme-linked immunosorbant assays), "sandwich" immunoassays, immunoradiometric assays, gel diffusion precipitation reactions, immunodiffusion assays, in situ immunoassays (e.g. using colloidal gold, enzyme or radioisotope labels, for example), Western blots, precipitation reactions, agglutination assays (e.g. gel agglutination assays, hemagglutination assays, etc.), complement fixation assays, immunofluorescence assays, protein A assays, and immunoelectrophoresis assays, etc.

As used herein, the term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies, enzyme linked antibodies, etc.

As used herein, the term "homologous recombination" refers to techniques utilizing the process of physical rearrangement of DNA involving the alignment of homologous sequences, crossover between the aligned DNA strands so as to produce an exchange of material between the strands. Homologous recombination is utilized to knock-out gene function or create deletion mutants. Methods for homologous recombination are well known and, for example, are described in U.S. Pat. No. 5,614,396, incorporated herein by reference.

The term "antigenic determinant" as used herein refers to that portion of an antigen that makes contact with an antibody (i.e. an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e. the "immunogen" used to elicit the immune response) for binding to an antibody.

The term "transgene" as used herein refers to a foreign, heterologous, or autologous gene that is introduced into a cell, cell line or organism. The term "foreign gene" refers to any nucleic acid (e.g. gene sequence) that is introduced by experimental manipulations and may include an autologous gene. The term "autologous gene" may encompass variants (e.g. polymorphisms or mutants) of the naturally occurring gene.

As used herein, the term "vector" is used in reference to nucleic acid molecules that transfer DNA segment(s) from one cell to another.

The term "expression vector" as used herein refers to a recombinant nucleic acid molecule that contains a desired nucleic acid target sequence and appropriate nucleic acid sequences necessary for the expression of nucleic acid or amino acid sequence in a host. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host" or "host cell" refers to any eukaryotic or prokaryotic cell (e.g. bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "sample" as used herein is used in its broadest sense. A sample suspected of containing a nucleic acid or amino acid sequence may comprise a cell, chromosomes isolated from a cell (e.g. a spread of metaphase chromosomes), genomic DNA (in solution or bound to a solid support), RNA (in solution or bound to a solid support), cDNA (in solution or bound to a solid support) and the like. A sample suspected of containing a protein may comprise a cell, a portion of a tissue, an extract containing one or more proteins and the like.

As used herein, the term "response," refers to the generation of a detectable signal when used in reference to an assay or other result (e.g. accumulation of reporter molecule, increase in ion concentration, accumulation of a detectable chemical product (e.g. antibody)).

As used herein, the terms "antagonist" and "antagonistic" refer to or describe a molecule which is capable of, directly or indirectly, substantially counteracting, reducing or inhibiting the biological activity or activation of PTHrP or its isoforms. In addition to the monoclonal antibodies, antagonist can include peptides of a partial sequence of PTHrP or one of its isoforms, preferably PTHrP1-173, and in particular a competitive antagonist of PTHrP 1-173 and its receptor. In addition, the PTHrP antagonist can be a non-peptidic compound that decreases the activity of PTHrP. The PTHrP antagonist can also be a compound inhibiting PTHrP signaling or signaling of one if its isoforms. The PTHrP antagonist can also be a compound inhibiting the specific PTHrP receptor for PTHrP 1-173. The PTHrP antagonist can also be a compound reducing the expression of PTHrP 1-173 or its receptor. A person skilled in the relevant art may understand that such a compound may include, for example, a molecule that could bind to the target PTHrP mRNA or the PTHrP gene or receptor. For example, such compounds can include siRNA or an antisense oligonucleotide or a specific compound or factor inhibiting PTHrP 1-173 mRNA. For example, it is known that PTH7-34 or PTHrP7-34 have been used as small peptide antagonists to block PTH or PTHrP action. Peptides derived from PTHrP1-173 can be used as an antagonist of PTHrP 1-173 and/or its receptor. The term PTHrP antagonist can be understood in its broad sense and include any compound that decreases the biological effects of PTHrP or one of its isoforms. In addition to the monoclonal antibodies of the present invention, antagonist can include peptides of a partial sequence of PTHrP and in particular a competitive antagonist of PTHrP 1-173. In addition, the PTHrP antagonist can be a non-peptidic compound that decreases the activity of PTHrP. Such compounds can be a siRNA or an antisense oligonucleotide or a specific factor inhibiting PTHrP 1-173 mRNA or its receptor.

As used herein, the term "antibody" or "Ab" is used in the broadest sense and specifically covers single anti-PTHrP monoclonal antibodies (including agonist, antagonist, and neutralizing or blocking antibodies) and anti-PTHrP antibody compositions with polyepitopic specificity. "Antibody" as used herein includes intact immunoglobulin or antibody molecules, polyclonal antibodies, multispecific antibodies (i.e. bispecific antibodies formed from at least two intact antibodies) and immunoglobulin or antibody fragments (such as Fab, F(ab').sub.2, or Fv), so long as they exhibit any of the desired agonistic or antagonistic properties described herein. Various procedures known within the art may be used for the production of polyclonal or monoclonal antibodies directed against a specific antigen, or against derivatives, fragments, analogs, homologs or orthologs thereof. While the invention has been demonstrated using mouse mAbs as preferred embodiments, the invention is not so limited. Such mAbs are within the scope of this invention. A person skilled in the relevant art will understand that the antibodies of the present invention also include chimeric, hybrid, or "humanized" antibodies, so long as they exhibit the desired biological activity or properties. Humanized mAbs using either human hybridomas or "dimeric antibodies" or other suitable method can be a preferable method for human therapeutic use. It will be understood by a person skilled in the relevant art that there are known techniques for creating chimeric or humanized antibodies. Since most available mAbs are of non-human origin, they are naturally antigenic in humans and thus can give rise to an undesirable immune response. It will be understood by a person skilled in the relevant art that the techniques for decreasing any undesirable immune response is generically termed "humanization".

Antibodies are typically proteins or polypeptides that exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

Antibodies, particularly of the IgM subclass, may inhibit tumor growth indirectly by mediating cytotoxicity via a targeting function: these mAbs belong to a subclass or isotype that upon complexing with the receptor activates serum complement and/or mediate antibody dependent cellular cytotoxicity (ADCC). Such antibodies may be used to induce lysis through the natural complement and to interact with ADCC on cells normally present. The ability of antibodies to mediate lysis of a patient's tumor cells can be tested in vitro by adding the antibody to the patient's tumor cells grown in vitro. The patient's own serum can then be used as a source of complement to test cytolysis of tumor cells in vitro. Those antibodies, including antibodies of the present invention such as, for example, antibodies that specifically bind to PTHrP1-173, that exhibit the highest level of cytolysis (through complement activation or ADCC) in vitro can then be administered to the patient for therapeutic ablation.

The selection of an antibody subclass selected for therapeutic purposes will depend on the expression of PTHrP or its isoforms in, on or by a tumor. If the tumor expresses high levels of the PTHrP1-173 isoform compared to normal tissues an IgM may be preferable to induce tumor cytolysis. However, if the PTHrP1-173 isoform is expressed at lower levels it may be preferable to use an IgG which is smaller and therefore more accessible to penetrate the tumor and also less cytotoxic for normal cells.

As used herein, "antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

As used herein, the term "variable domain" describes certain portions of antibodies that differ in sequence among antibodies and are used in the binding and specificity of each particular antibody for its particular antigen. However, the variability is not usually evenly distributed through the variable domains of antibodies. It is typically concentrated in three segments called complementarity determining regions ("CDRs") or hypervariable regions both in the light chain and the heavy chain variable domains. The more highly conserved portions of the variable domains are called the framework regions ("FR"). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term "monoclonal antibody" or "mAb" refers to an antibody obtained from a population of substantially homogeneous antibodies, i.e. the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method.

It will be understood by a person skilled in the relevant art that modifications of the antibodies of the present invention are contemplated herein. The antibodies of the present invention may be modified by conjugating, tagging or labeling through methods known in the art, the antibodies of the present invention to any known diagnostic or therapeutic agent, including but not limited to cytotoxic agents (e.g. immunotoxin conjugates), prodrugs, drugs (e.g. pharmaceutically active substances) or other effector molecules which are effective in the treatment of disease as well as known reporter molecules. Such modified antibodies, also referred to as immunochemical derivatives thereof include, but are not limited to (a) labeled (e.g. radiolabeled, enzyme-labeled, fluorochrome or chemiluminescent compound) monoclonal antibodies of the present invention, preferably humanized mAbs, for diagnosing or detecting tumors and tumor spread (e.g. metastasis) using known imaging technologies; and (b) immunotoxin conjugates of the mAbs of the present invention, preferably humanized mAbs, where the mAbs of the present invention are conjugated to known cytotoxic, radioactive, radiolabelled, prodrug or drug moieties (e.g. radioimmunotherapy). It will be understood by a person skilled in the relevant art that the term "cytotoxic agent", "cytotoxins" or "cytotoxic" as used herein generally refer to a substance that inhibits or prevents the function of cells and/or causes destruction of cells and includes, but is not limited to, radioactive isotopes, chemotherapeutic agents, and toxins such as small molecule toxins or enzymatically active toxins of bacterial, fungal, plant or animal origin, including fragments and/or variants thereof. It will also be understood by a person skilled in the relevant art that the term "prodrug" as used in this application generally refers to a precursor or derivative form of a pharmaceutically active substance that is less cytotoxic to target cells compared to the pharmaceutically active substance and is capable of being activated or converted into the more pharmaceutically active substance.

As used herein, "hybridoma" refers to cell lines that have been engineered to produce a monoclonal antibody, such as made by the hybridoma method first described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that may specifically bind to the immunizing agent. The lymphocytes are then fused with an immortalized cell line using a suitable fusing agent, such as polyethylene glycol, to form a hybridoma cell. See, for example, Goding, Monoclonal Antibodies: Principles and Practice, Academic Press, (1986) pp. 59-103 or Hardy R R et al. In Handbook of Experimental Immunology (DM Weir Ed) Blackwell Scientific p13.1, the contents of which are incorporated by reference. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if cells lack the enzyme hypoxanthine guanine phosphoribosyl transferase (HGPRT or HPRT), the culture medium for the hybridomas typically may include hypoxanthine, aminopterin, and thymidine ("HAT medium"), which substances prevent the growth of HGPRT-deficient cells.

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem. 107:220 (1980). It is an advantageous to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

It may be understood by a person skilled in the relevant art that monoclonal antibodies of the present invention can also be made by recombinant DNA methods, such as those described in U.S. Pat. No. 4,816,567, which is hereby incorporated by reference. DNA encoding the monoclonal antibodies of the invention can be readily isolated and sequenced using conventional procedures (e.g. by using oligonucleotide probes that are capable of binding specifically to genes encoding the heavy and light chains of murine antibodies). Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

As used herein, the term "knock out" and "knock down" generally refer to functionally eliminating the expression of a gene product or reducing the expression thereof to determine the gene products function. It may be understood by a person skilled in the relevant art that the term functionally eliminating expression may refer to either completely eliminating expression thereof or decreasing expression thereof beyond a detectable limit. The term "knock out animal" as used herein may be understood to generally refer to a transgenic animal in which a polynucleotide transgene sequence (i.e. a gene or a cDNA) that the animal does not naturally have in its genome is inserted into the genome so as to decrease, eliminate or otherwise "knock out" the production and/or expression of the endogenous gene product. The term double knock out may be understood to mean a "knock out" where both alleles of the gene of interest has been knocked out. Such animals are useful for the in vivo study, testing and validation of, intra alia, the function of the product encoded by the polynucleotide sequence. It may be generally understood by a person skilled in the relevant art that "knock down" can refer to inhibition via siRNA methods employed in vivo or in vitro (e.g. cell lines).

It will be understood by a person skilled in the relevant art that the compositions of the present invention, including but not limited to antibodies and siRNA, can be formulated into pharmaceutical compositions for administration in a manner customary for administration of such materials using standard pharmaceutical formulation chemistries and methodologies, all of which are readily available to a person skilled in the relevant art. It will also be understood by a person skilled in the relevant art that such pharmaceutical compositions may include one or more excipients, carriers, stabilizers or other pharmaceutically inactive compounds, such as, but not limited to, wetting or emulsifying agents, pH buffering substances and the like. Pharmaceutically acceptable salts can also be included therein. A thorough discussion of pharmaceutically acceptable excipients, vehicles and auxiliary substances is available in *Remington's Pharmaceutical Sciences* (Mack Pub. Co. N.J. 1991), incorporated herein by reference. Such pharmaceutical compositions can be prepared as injectable or oral preparations. The antibodies of the present invention may be administered by injection, including, but not limited to, intramuscular, intravenous, subcutaneous, peritoneal, transdermic or nasal injection. The therapeutically effective doses may vary according to body weight and the timing and duration of administration will be determined by specific clinical research protocols.

The description that follows, and the embodiments described therein, are provided by way of illustration of an example, or examples, of particular embodiments of the principles and aspects of the present invention. These examples are provided for the purposes of explanation, and not of limitation, of those principles and of the invention. In the description, like parts are marked throughout the specification and the drawings with the same respective reference numerals.

The present invention is directed to the diagnosis, treatment and inhibition of tumor growth and its progression to metastatic sites through the inhibition of the production of PTHrP or PTHrP signaling and preferably the specific isoform PTHrP1-173 as a treatment for disease, including several types of cancers. More preferably, the present invention is directed to methods of inhibiting the receptor and/or its signaling pathways activated by the specific isoform PTHrP1-173. The invention is also directed to in vivo imaging and therapeutic targeting of tumors and metastatic sites expressing PTHrP and its isoforms, preferably the specific isoform PTHrP1-173, using monoclonal antibodies directed to the PTHrP and its isoforms, such monoclonal antibodies being preferably tagged or labelled with diagnostic (e.g. a reporter molecule) or therapeutic agent (e.g. cytotoxic agent, prodrug or drug). The invention is also directed to the detection of isoforms of PTHrP as indicators of disease activity or metastatic spread, preferably prior to the development of hypercalcemia, or as prognostic indicators of possible treatments. The invention may be applicable to many disease states, including but not limited to several types of cancer (such as breast, lung, prostate, melanoma and squamous of several types) expressing these isoforms, alone or in combination with other therapeutic agents.

Inhibition of PTHrP and its isoforms was tested in vitro and in vivo in an array of human cancer models including breast cancer, melanoma, squamous cancer, prostate cancer as described herein. The methods of the present invention are directed to blocking the production/activity of PHTrP through an antagonist of PHTrP or its isoforms, preferably the specific isoform PTHrP 1-173. Such methods include, but are not limited to, homologous recombination (double knock-out), siRNA knockdown and include such antagonists as monoclonal antibodies directed thereagainst as well as peptide fragments which could bind to receptors and block the activity of the specific isoform PTHrP1-173.

EXAMPLES

Example 1

Production, Preparation and Characterization of Anti-PTHrP1-33, 140-173 and 151-169 Monoclonal Antibodies Mouse monoclonal antibodies were produced from hybridomas through cell fusion between myeloma cells and antibody producing spleen cells derived from mice immunized with antigens derived from PTHrP and its isoforms. The antigens that were chosen were either unique to the PTHrP isoform 1-173 (derived from C-terminal fragments) or common to all human PTHrP isoforms (derived from N-terminal fragments).

Preparation of Antigens

According to the present invention, the antigens used for immunization included the following peptides: (a) human PTHrP140-173 ("hPTHrP140-173") and human PTHrP151-169 ("hPTHrP151-169"); and (b) human PTHrP1-33 ("hPTHrP1-33"). It will be understood that the hPTHrP140-173 antigen is a polypeptide comprising the amino acid residues at amino acid position Nos. 140 to 173 of the isoform PTHrP1-173 and similarly the hPTHrP151-169 antigen is a polypeptide comprising the amino acid residues at amino acid position Nos. 151 to 169 of the isoform PTHrP1-173. It will be understood that the hPTHrP1-33 antigen is a polypeptide comprising the amino acid residues at amino acid position Nos. 1 to 33 of PTHrP, which is common to all three of the human isoforms. It will be understood by a person skilled in the relevant art, therefore, that the antigens hPTHrP140-173 and hPTHrP151-169 are specific to the isoform PTHrP1-173. Any antibodies raised to these antigens based on the protocols outlined below were directed to epitopes on the isoform PTHrP1-173. On the other hand, it will be understood by a person skilled in the relevant art that the antigen hPTHrP1-33 is common to all three isoforms hPTHrP. As such, any antibodies raised to the hPTHrP1-33 antigens based on the protocols outlined below were directed to epitopes on all three of the human isoforms of PTHrP.

Immunization and Collection of Antibody Producing Cells.

Synthetic human hPTHrP1-33, hPTHrP140-173 and hPTHrP151-169 were purchased from Sheldon Biotechnology Centre (McGill University, Montreal). The hPTHrP140-173, hPTHrP151-169 and hPTHrP1-33 antigens were mixed with 50% (v/v) Freund's complete adjuvant prior to injection into mice as outlined below.

Female 5-6 week old BALB/C mice were injected intraperitoneally with 25 µg of one of the hPTHrP140-173, hPTHrP151-169 or hPTHrP1-33 antigens emulsified with 50% (v/v) Freund's complete adjuvant. The mice were given a booster dose of the relevant antigen in 50% (v/v) Freund's incomplete adjuvant, namely the antigen previously injected in the mice 13 to 15 days subsequent to the first injection of the relevant hPTHrP antigen. One week following the booster injection of the hPTHrP antigen, sera were collected from the immunized mice by tail bleeding to determine the presence of antibodies against the antigen used to immunize that particular mouse using ELISA (enzyme linked immunosorbent assay). Mice producing antibodies to each of the hPTHrP140-173, hPTHrP151-169 or hPTHrP1-33 antigens were then injected with a further 25 µg of corresponding or relevant hPTHrP antigen. Three days after final immunization spleen cells were collected from the mice receiving the final immunization.

Cell Fusion

The monoclonal antibodies were prepared according to the method of (Hardy R R et al. In Handbook of Experimental Immunology (D M Weir Ed) Blackwell Scientific p13.1). The spleens were removed surgically and spleen cells of antibody producing animals immunized with one of the hPTHrP140-173, hPTHrP151-169 or hPTHrP1-33 antigens were isolated by known methods and gently flushed using serum-free RPMI-1640 at 37° C. The isolated spleen lymphocytes were then mixed with myeloma cells Sp2 or FO (both from ATCC, Rockville, Md.), and fused using 50% polyethylene glycol 1500 (Merck, Darmstadt, Germany) according to known methods. The resulting fusions cells were then cultured in pre-cultured 96 well tissue culture plates (Becton Dickinson Labware, Franklin Lakes, N.J.) (Immunolon, Dynex, Va., USA) with normal mouse spleen lymphocytes in a hybridoma selection medium consisting of RPMI supplemented with 20% FBS, antibiotic-antimycotic mixture and 1× hypoxanthine-aminopterin-thymidine (HAT) medium (Gibco BRL) at 37° C. in the presence of 5% $CO_2$. On day 4 and 8 of the incubation, the HAT medium was replaced with fresh HAT medium.

Selection and Cloning of mAb Secreting Hybridomas

Following the spleen lymphocyte and myeloma cell fusion, antibody secreting hybridomas were selected and cultured using selective growth and then screened by limited dilution. Supernatants from hybridoma cell cultures were screened for antibodies specific to one of the three antigens used, namely hPTHrP140-173, hPTHrP151-169 or hPTHrP10-33 after 13 to 15 days of culture using 96 well flat bottom microtiter plates (VWR, Mississauga, ON) precoated with corresponding peptides by ELISA using a secondary goat anti-mouse IgM+IgG+IgA (H+L) antibody conjugated with horseradish peroxidase (HRP) (Southern Biotech, Birmingham, Ala.) and ABTS peroxidase substrate (KPL Inc, Gaithersburg, Md.). Selected hybridomas were cloned twice using limiting dilution. Positive hybridoma clones were first propagated in 24 well plates and upon reaching confluence transferred to T75 flasks after a second ELISA testing.

Collection of Monoclonal Antibodies

The hybridomas identified as producing desired antibodies were adapted to BD cell medium through progressively adding amounts of the BD cell medium to the existing cell medium until the cells were subsequently transferred into Celline flask (BD Biosciences, San Diego, Calif.), and cultured in BD cell medium to produce monoclonal antibodies (mAb) in cell supernatant. Supernatant was centrifuged at 2000 g for 5 min to remove the cellular debris and supernatant filtered through 0.22-0.45 µm filters to further eliminate cell debris, aliquoted and kept at 4° C. Affinity purification of the mAbs was done using a protein G Sepharose column (Amersham Pharmacia Biotech, Baie d'Urfe, Quebec, Canada) and quantified using a protein assay kit (Pierce, IL, USA). Purified antibodies were concentrated to 1-5 mg/ml, dialyzed against PBS, and stored at −70° C. mAbs isotyping was determined using a commercial isotyping kit (BioRad, USA).

As shown in FIG. 5, the following hybridoma clones were obtained. Hybridoma No. 158 and No. M45 produced monoclonal antibodies (mAb158 and mAbM45) exhibiting a strong binding ability to hPTHrP1-33, an N-terminus fragment of PTHrP. Hybridoma No. 104 and No. M18 produced monoclonal antibodies (mAb104 and mAbM18) exhibiting a strong binding ability to PTHrP 140-173, a C-terminus fragment of PTHrP. Hybridoma No. 6 produced monoclonal antibodies (mAb6) exhibiting a strong binding ability to PTHrP 151-169, a C-terminus fragment.

Hybridomas Nos. 104, M18 and 6, produced monoclonal antibodies mAb104, mAbM18 and mAb6 respectively, have been deposited with the International Depositary Authority of Canada (IDAC), of the National Microbiology Laboratory, Health Canada located at 1015 Arlington Street, Winnipeg, Canada, R3E 3R2, on Aug. 15, 2007, and have been granted Accession Nos. 150807-02, 150807-03 and 150807-01, respectively.

It may be understood by a person skilled in the relevant art that monoclonal antibodies of the present invention can also be obtained using ascite formation and other conventional cell culture or molecular biology methods known in the art. In the ascite formation method, the hybridomas are inoculated intra-peritoneally into female BALB/c nude mice and the asictes collected after 1-4 weeks.

Monoclonal Antibody Subclasses

Monoclonal antibody subtyping was determined using a commercial isotyping kit (Bio-Rad, USA). The subclasses characterization of the monoclonal antibodies against PTHrP1-33, PTHrP140-173 and PTHrP151-169 in FIG. 5. As seen in FIG. 5, there is shown a table representing the characterization of PTHrP antibodies subclasses against the different isoforms. As shown in FIG. 5, there were identified three monoclonal antibodies specific to the PTHrP1-173 isoform; (i) mAb104; (ii) mAbM18; and (iii) mAb6. The monoclonal antibodies of the present invention comprise the following subclasses: (i) IgM kappa for mAbM18 and mAbM45; (ii) IgG2b kappa for mAb104; (iii) IgG1 kappa for mAb6; and (iv) IgG3 for mAb158 (see FIG. 5). The specificity of these monoclonal antibodies was tested subsequently using ELISA, Western blots and immunohistochemistry as described in greater detail below.

Evaluation of Antigen Binding and Neutralizing Activity of Monoclonal Antibodies Determination of Antibody Concentration The concentration of the purified antibody was determined by ELISA. ELISA was used to determine the concentration of each monoclonal antibody as follows. 100 µl of one of hPTHrP1-33, hPTHrP140-173 or hPTHrP151-169 antigens prepared at a concentration of 5 µg/ml was immobilized to each well of a 96 well plate for ELISA. After blocking with 200 µl of a diluting buffer (1% BSA) known concentrations of the corresponding purified (by affinity purification using a protein G Sepharose column as described earlier) monoclonal antibody were used as standards. To determine the concentration of monoclonal antibodies in subsequent preparations a stepwise diluted supernatant of monoclonal antibody was added to each well followed by addition of an horseradish peroxidase (HRP) conjugated anti mouse IgG (M) antibody and 100 µl of substrate solution after which absorbance at 405 nm is measured. Monoclonal antibody concentration of each specific antibody was determined against the standards preparations of each specific purified monoclonal antibody.

Determination of Antigen Binding Activity

Figure 6:
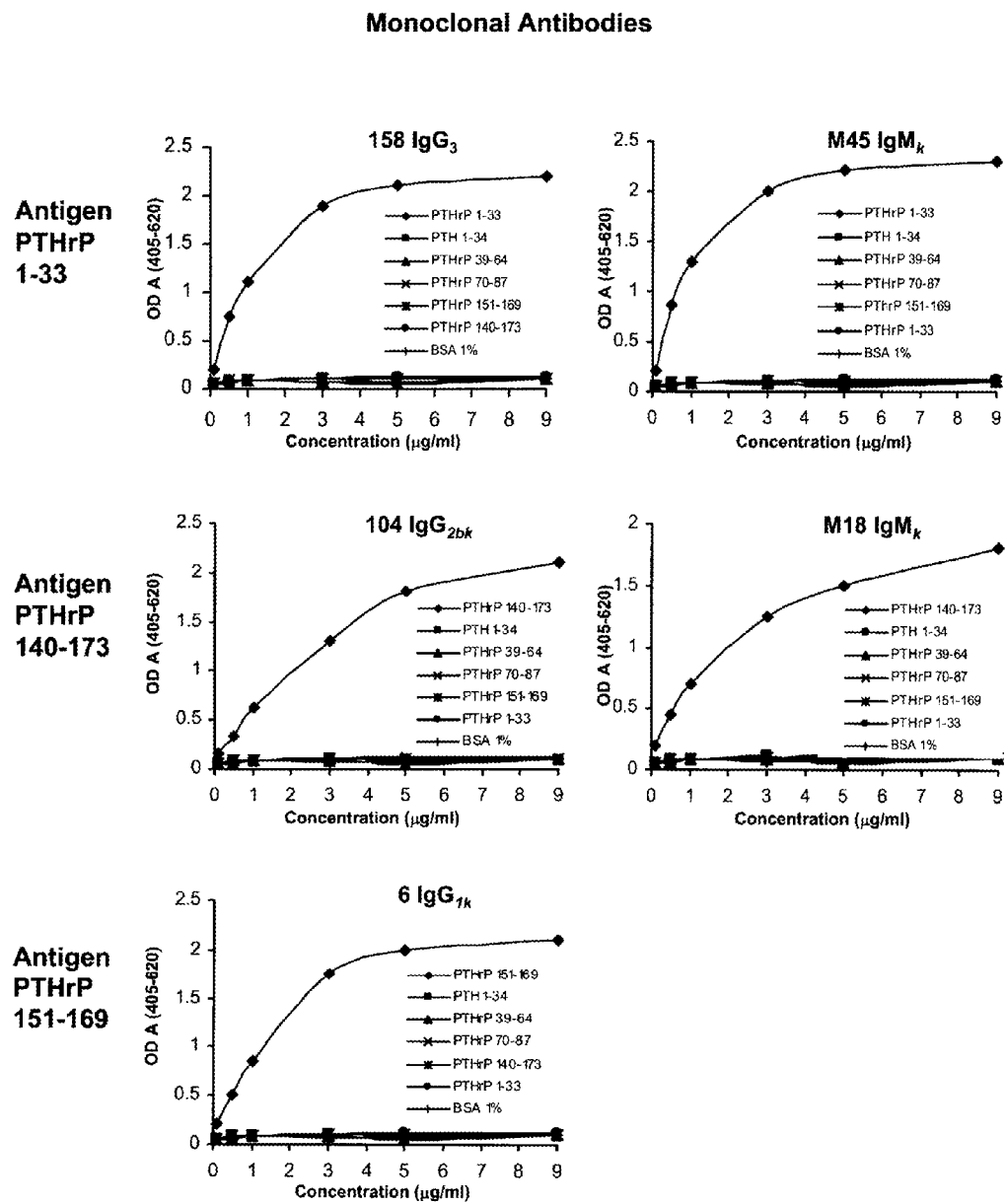
FIG. 6 is a graph showing the measurement of the antigen-binding activity of the antibodies of the present invention by ELISA.
Figure 7:
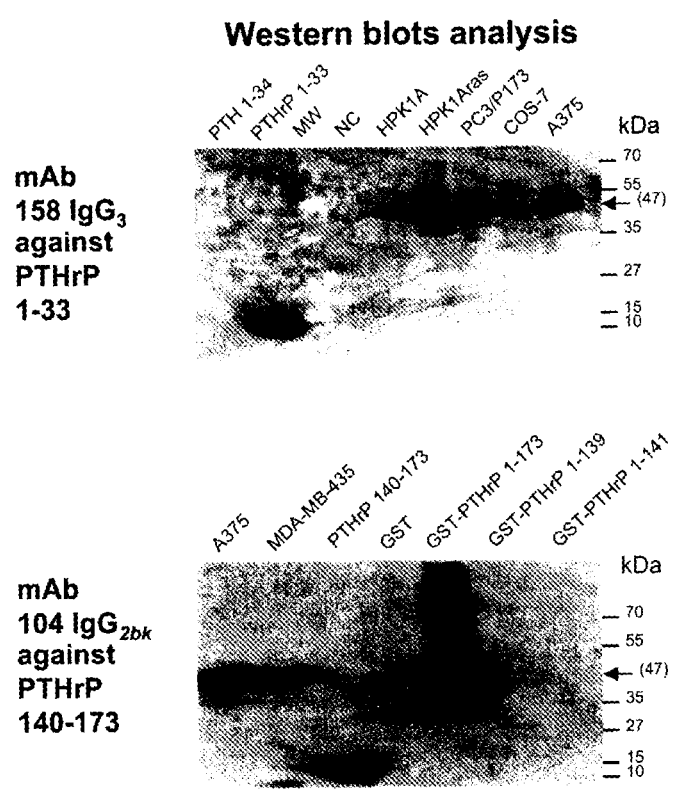
FIG. 7 is a Western blot demonstrating the specific recognition of antigens by the monoclonal antibodies of the present invention.
Figure 8:
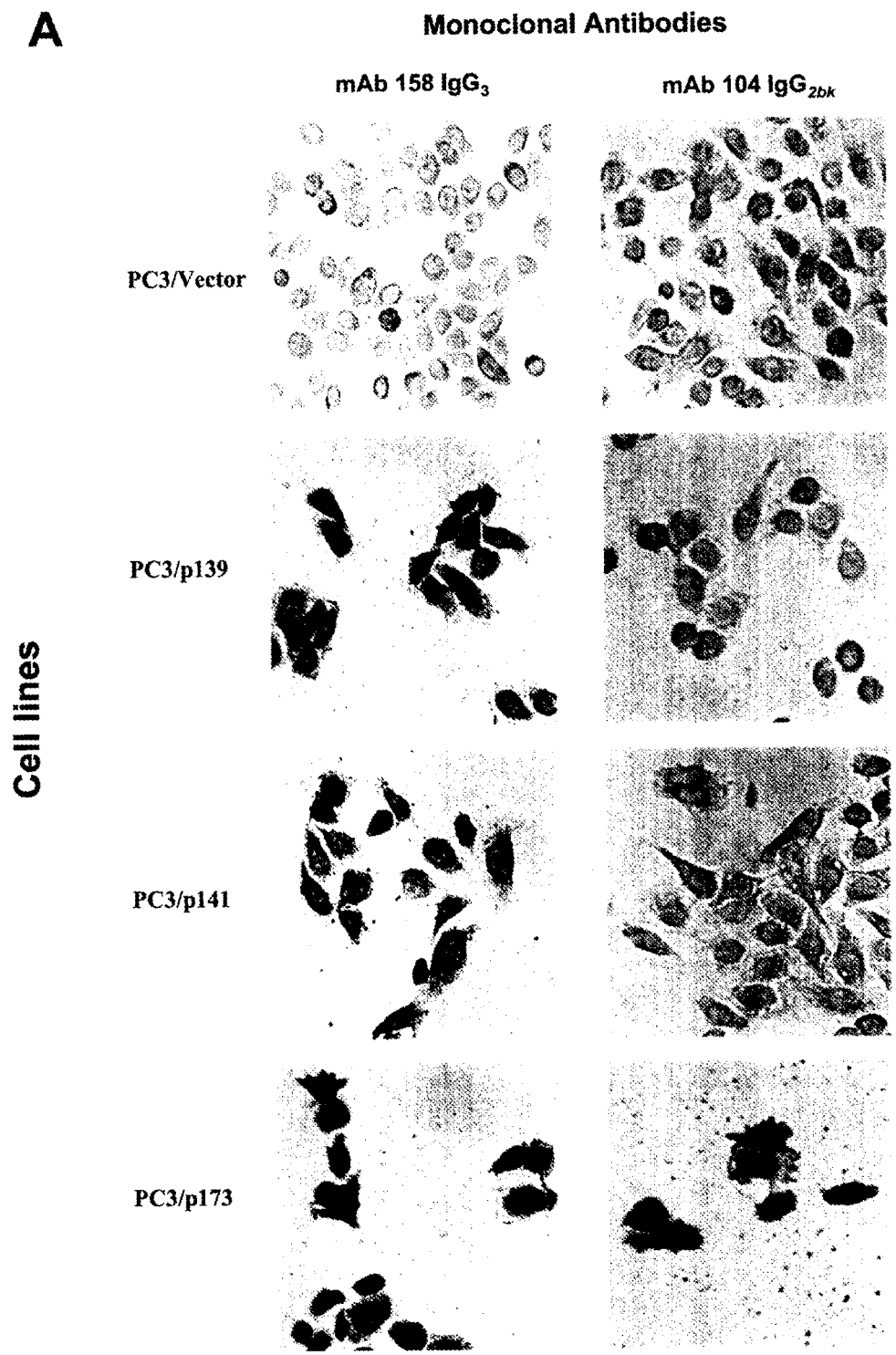
FIGS. 8(A) & (B) show the immunohistochemistry of PC-3 prostate cancer cells in tissue culture in vitro (A) and tissue sections of A375 melanoma cells metastasis to lymph nodes in vivo (B). Cells or tissues were immunostained with monoclonal antibodies of the present invention directed at either PTHrP1-33 or PTHrP140-173.
Figure 8:
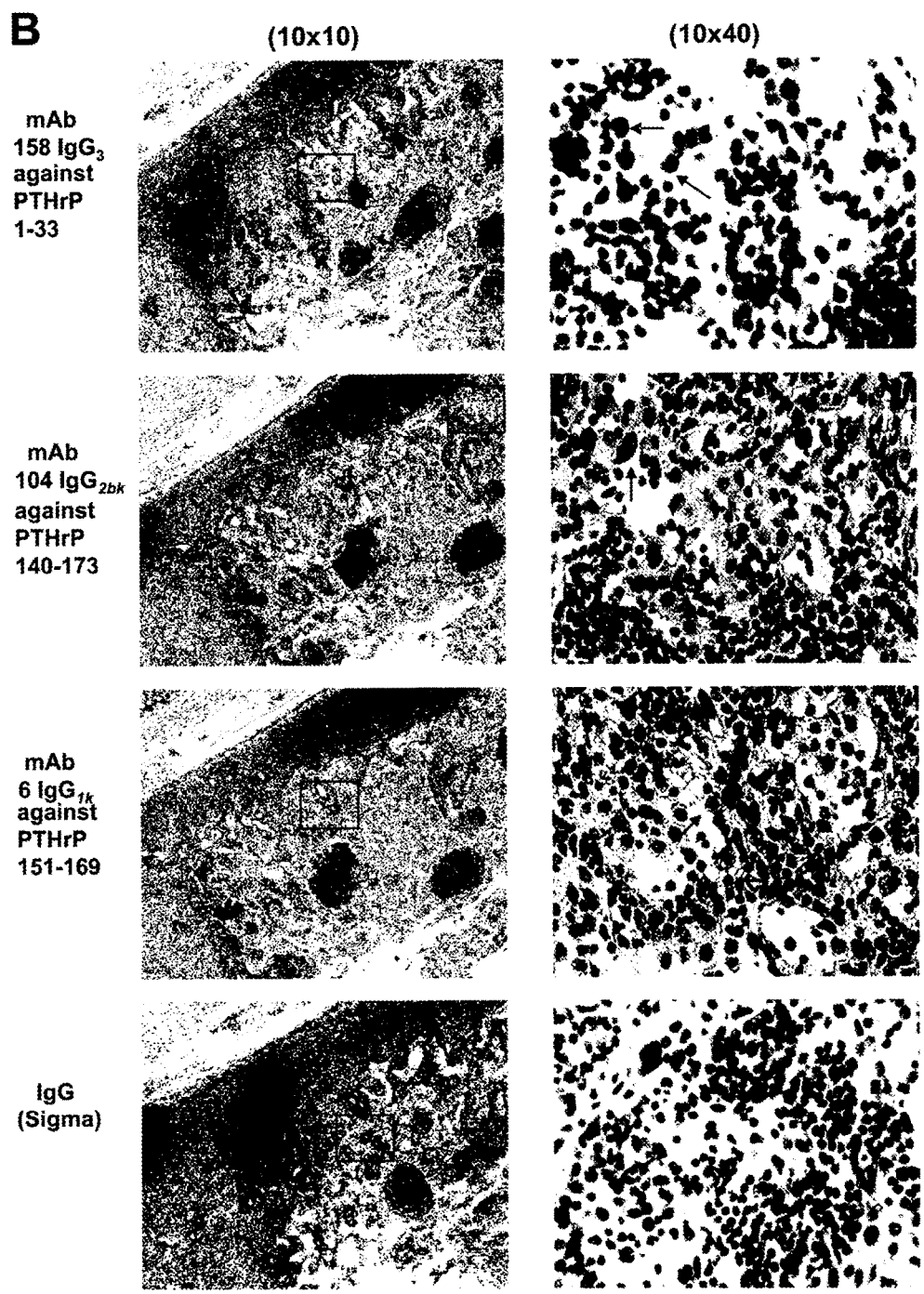

ELISA plates for determining the antigen binding ability are prepared as follows. One of hPTHrP1-33, hPTHrP140-173 or hPTHrP151-169 antigens prepared at a concentration of 1-10 µg/ml were immobilized to each well of a 96 well plate for ELISA. After blocking with 200 µl of a diluting buffer (1% BSA), a stepwise diluted supernatant of monoclonal antibody was added to each well followed by addition of an horseradish peroxidase (HRP) conjugated anti mouse IgG (M) antibody and 100 μl of substrate solution after which absorbance at 405 nm is measured. FIG. 6 shows specific antigen/antibody interaction by ELISA. As described in greater detail herein, mAbs of the present invention raised against the specific antigens were found to be highly specific to each antigen and no cross-reactivity between antibodies and the other antigens was observed. Specific recognition of the antigens with the monoclonal antibodies was also demonstrated by western blot analysis (see FIG. 7). FIG. 7 shows a Western blot demonstrating the specific recognition of antigens by monoclonal antibodies of the present invention. The mAb104 is directed against and recognizes PTHrP140-173; mAb104 is highly specific for the PTHrp1-173 isoform as seen in FIG. 7, and no cross-reactivity was observed with PTHrP1-139 or PTHrP1-141 isoforms. FIGS. 8 (A) & (B) show the immunohistochemistry of PC3 prostate cancer cells in tissue culture in vitro (see FIG. 8(A)) and tissue sections of A375 melanoma cells metastasis to lymph nodes in vivo (see FIG. 8(B)). As shown in FIG. 8(A), cells were immunostained with monoclonal antibodies of the present invention directed at either PTHRP1-33 (mAb158) or PTHRP140-173 (mAb104). Note that only PC3 stably transfected with a construct of the present invention expressing PTHrP1-173(PC3/p173) were recognize by mAb104 whereas PC3 cells overexpressing any isoform was recognize by mAb158.

Example 2

Mouse Model of Human Metastatic Melanoma.

The incidence of melanoma has increased steadily over the past several decades (Hall H I et al J Am Acad Dermatol (1999) 40, 35) and the survival of patients once melanoma cells have invaded the basement membrane is extremely poor (Shields J D et al Br J Cancer (2004) 90, 693). Treatments for melanoma at such a stage are very limited and the response is not satisfactory. The present invention involves the use of a human melanoma model (A375) in which PTHrP is overexpressed (El Abdaimi et al Am J Physiol (2000) 279, C1230) to provide a treatment for melanoma. A375 is known to produce all three isoforms of PTHrP. Various antagonists of the present invention were test against this model.

Figure 11:
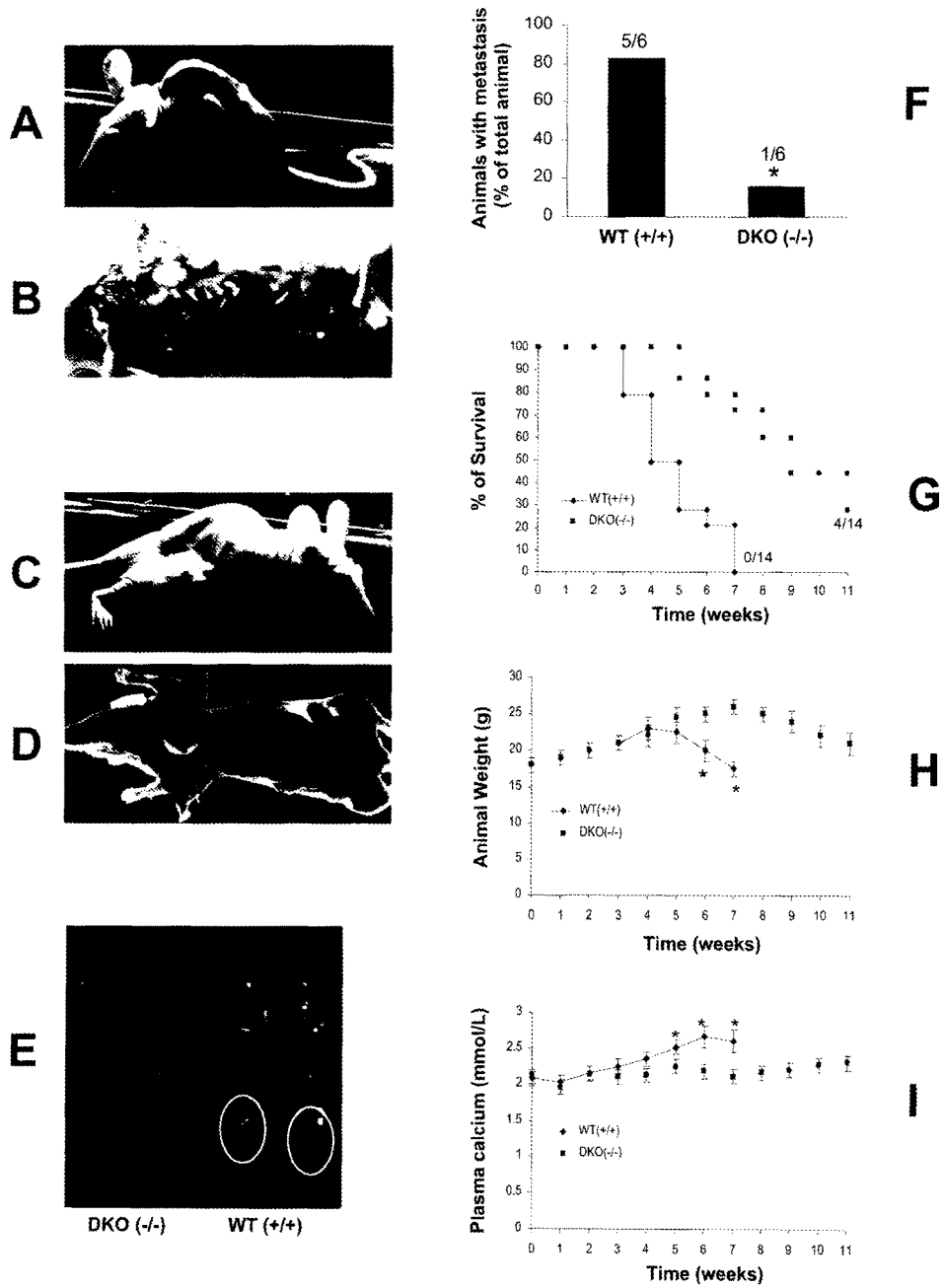
FIGS. 11(A) to (I) show the effect of PTHrP inhibition of all three isoforms in A375 human melanoma cells on animal well-being ((A, WT+/+)) & ((C, DKO−/−)), lymph node invasion ((B, WT+/+)) & (D, DKO−/−)), bone matastasis by fluorescence imaging ((E) & (F)), on animal survival by Kaplan Meier analysis (G), animal weight (H) and circulating calcium concentrations (I). The asterisk (*) indicates a statistically significant difference between A375 DKO(−/−) and A375 WT(+/+) animals' metastatic spread, survival, weight and circulating calcium levels (p≤0.01).

As shown in FIGS. 9 to 11, when antagonists of the present invention are used to target all three isoforms, there is demonstrated a striking reduction in tumor growth and metastasis in vivo (see FIGS. 9 & 11) and invasion in vitro (FIG. 10).

FIG. 9 describes the number of animals who developed metastasis at a specific site over the total number of animals transplanted with A375 cells into the left cardiac ventricle at sacrifice. In animals transplanted with PTHrP knockout A375 cells (DKO−/− A375), a striking reduction in metastatic spread by over 50% was observed at all sites except bone where the reduction was only 20%. However, when metastatic bone lesions were analyzed are earlier time by fluorescence imaging (of GFP-labeled A375 cells) using the eXplore Optix instrument, a striking reduction in the incidence of metastatic lesions was observed at earlier time points (9 and 14 days post tumor implantation) in DKO−/− A375 animals (see FIGS. 11 (E) & (F)).

The reduction of metastasis to lymph nodes is clearly demonstrated at autopsy in DKO−/− A375 animals (see FIG. 11(D)). Note the single lesion detected by fluorescence imaging) as compared to wild type WT+/+A375 animals in which multiple lymph node metastasis are visible macroscopically, as shown in FIG. 11(B). Animal well-being and maintenance of weight was also preserved in DKO−/−A375 animals as compared to wild type WT+/+A375 animals (as shown in FIGS. 11(A), (C) & (H)). Also note that circulating concentrations of calcium remained normal in DKO−/−A375 animals but increased over time in wild type WT+/+A375 animals (see FIG. 11(I)).

In both models, metastasis can be visualized following implantation of tumor cells stably transfected with green fluorescent protein (GFP). As shown in FIG. 11(E), in vivo imaging of bone metastasis can be done with the eXplore Optix instrument (GE/ART). This technology permits early detection of bone metastasis prior to visible lesions on X-rays and can be used to easily monitor the progression of bone metastasis as well as other metastatic sites during therapeutic intervention such as monoclonal antibodies of the present invention. A typical fluorescence imaging of bone metastatic lesions is shown in FIG. 11(E) and demonstrate an inhibition of bone metastatis in animals implanted with DKO−/−A375 cells as compared to wild type WT+/+A375 animals.

Furthermore, the survival of animals was significantly prolonged following PTHrP knockout in animals transplanted A375 tumor cells (see FIG. 11 (G)). The effect of PTHrP inhibition of all three isoforms by homologous recombination (DKO−/−) in A375 human melanoma cells shows increased animal survival by Kaplan Meier analysis. This survival advantage is demonstrated in mice transplanted into the left ventricle with A375 cells knockout cells (DKO−/−) as compared to animals transplanted with wild type cells (WT+/+) (see FIG. 11(G)).

FIGS. 10(A) & (B) show the results of PTHrP inhibition of all three isoforms by homologous recombination (double knock-out, DKO−/−) to disrupt both alleles of the PTHrP gene in A375 human melanoma cells. Cell growth (see FIG. 10(A)) and invasion in vitro (see FIG. 10(B)) was then determined. As shown in FIGS. 10(A) & (B), there is inhibition of cell growth and invasion in A375 knockout cells (DKO−/−) as compared to wild type cells (WT+/+) transfected with vector alone ($p \leq 0.001$).

In subsequent experiments, the efficiency of a monoclonal antibody directed at the N-terminal end of PTHrP (and therefore recognizing all isoforms) to the specific monoclonal antibody directed at the C-terminal end specific against the PTHrP1-173 isoform were compared. The efficacy of these antibodies on cell growth and invasion in vitro was similar (see FIG. 12).

Figure 12:
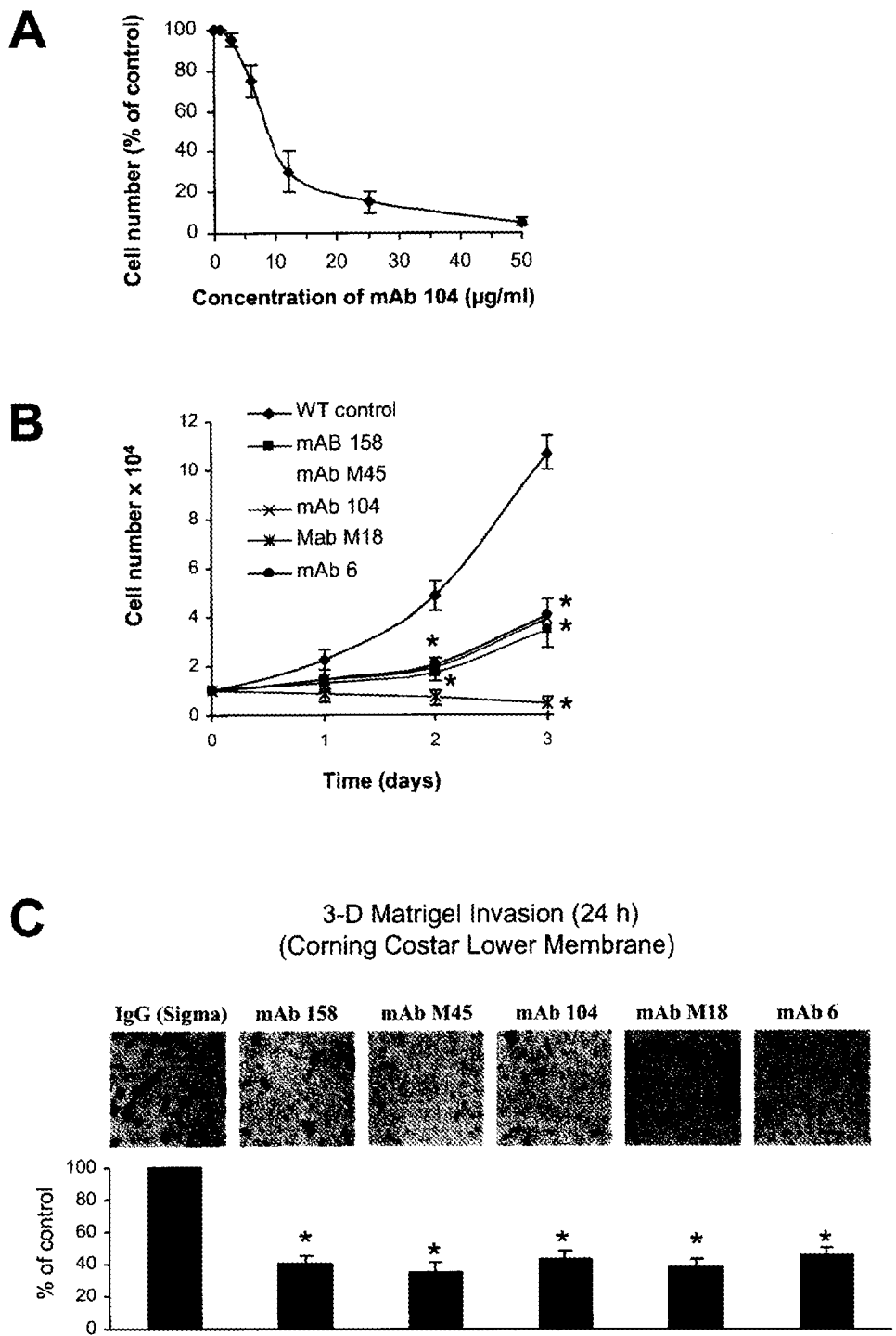
FIGS. 12(A) to (C) show the effect of the neutralizing activity of the monoclonal antibodies on cell growth and invasion of A375 cells. The asterisk (*) indicates a statistically significant difference between A375 wild type cells treated with vehicle (WT control, IgG) and cells treated with the various mAbs (p≤0.01).

FIG. 12 shows the effect of the neutralizing activity of monoclonal antibodies of the present invention on cell growth and invasion of A375 cells. FIG. 12(A) shows the determination of the optimal mAb concentration, while FIG. 12(B) shows the effect of the various mAb on cell growth. FIG. 12(C) shows the effect of the various mAb on invasion. Furthermore, in vitro knock-down of all PTHrP isoforms by siRNA of the present invention reproduced all the effects seen with the monoclonal antibodies, as shown on FIG. 13. FIG. 13 shows the effect of the neutralizing activity of siRNA against all PTHrP isoforms on cell growth and invasion of A375 cells. As shown in FIG. 13(A) there is provided tumor cell growth or velocity over time, while FIG. 13(B) shows invasion through matrigel. Note the significant inhibition with siRNA knockdown on growth and invasion ($p \leq 0.01$).

The human amelanotic melanoma cell line A375 (ATCC) was transplanted into nude mice and the therapeutic efficacy of the monoclonal antibodies examined on tumor growth and metastasis. These human cells can be transplanted either subcutaneously to examine tumor growth or into the left cardiac ventricle to examine metastasis. Metastasis to multiple organs including lungs, liver, bone, heart and lymph nodes develop rapidly within 5 weeks post-tumor transplantation and the animals invariably die within 7-8 weeks.

Therapeutic efficacy of the monoclonal antibodies on tumor growth following implantation of tumor cells subcutaneously were tested in 4-5 week old female athymic nude mice (BALB/c-nu/nu, Charles River). $1\times10^6$ of melanoma A375 cells were suspended in 100 µl of PBS and subcutaneously implanted in female nu/nu mice (Charles River, St. Constant, QC). Treatment was initiated 1 day after cell inoculation using 100 µg of antibodies injected subcutaneously every 2 days for 5 weeks. Control animals were injected with 100 µg of non-immune IgM or IgG (Sigma) every 2 days for 5 weeks. The rate of primary tumor growth was determined by plotting the means of two orthogonal diameters of the tumors, measured at 5-day intervals. Three-dimensional tumor measurements were done using FST calipers (Switzerien). Tumor diameter long axis (L) and mean mid axis width (W) were measured to estimate the tumor volume (V) using the following formula:

$$V = \frac{4}{3}\pi \times \frac{L}{2}\left(\frac{W}{2}\right)^2$$

Growth curves were generated by plotting the mean tumor volume of mice. Treatment of these animals with monoclonal antibodies directed either at the N-terminal end or the C-terminal end significantly delayed tumor onset and progression (see FIGS. 14(A) to (C)). As seen in FIGS. 14(A) to (C), there is shown the effect of monoclonal antibodies of the present invention in vivo on tumor growth in nude mice transplanted with A375 cells subcutaneously. (A) Tumor volume over time. (B) Photographs of the tumors excised at sacrifice. (C) Tumor weight (mean±SEM) of tumors shown in (B). (D) Hematoxylin and eosin ("H&E") staining of a tumor (vehicle alone) excised at sacrifice. The mAbM18 (directed against PTHrP140-173) and mAb158 (directed against PTHrP1-33) showed the greatest effect with a reduction of over 75% of tumor growth and weight as compared to controls (see FIGS. 14 (A), (B) & (C)). The other mAbs (mAb104, mAb6 and mAbM45) reduced tumor growth by 30-40%. FIG. 14(D) shows the H&E staining of typical A375 melanoma cells from a tumor excised at sacrifice.

The effect of the monoclonal antibodies on the metastatic spread of tumor cells was examined following intra-cardiac injection of A375 cells. Intracardiac injection of human melanoma cells A375 was performed according to the procedure described previously in the relevant art (Sasaki et al Cancer Res (1995) 55, 3551). $5\times10^5$ A375 cells were suspended in 0.1 ml of PBS and then injected into the left cardiac ventricle of female nude mice (BALB/C nu/nu), using a 27-gauge needle under anesthesia. Animals were monitored every 5 days for up to 50 weeks for tumor growth and general health. Antibody treatment as noted herein was initiated 1 day after cell inoculation. 100 µg of antibodies were injected subcutaneously, every 3 days for up to 20 weeks. Control animals were injected with 100 µg of non-immune IgG or IgM (e.g. IgM or IgG that was not derived from an animal immunized with the PTHrP isoforms) every 3 days for up to 20 weeks. Control mouse non-immune antibodies IgG and IgM were obtained from Sigma (St. Louis, Mo., USA) and were desalted with Centricon columns (Millipore, Bedford, Mass., USA) prior to use. Other control animals were injected with supernatant from hybridoma cell cultures derived from non-immunized mice.

When animals were sacrificed, lesions size and number of tumors were analyzed in liver, lungs, bones, lymph nodes, heart, spleen and pancreas and kidney. Animal survival was determined by Kaplan Meyer analysis, well known in the art.

Figure 15:
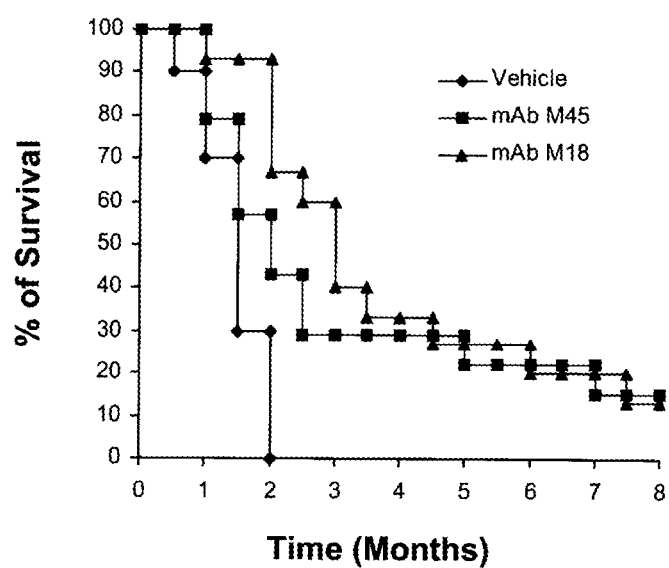
FIGS. 15(A) & (B) show the effect of monoclonal antibodies of the present invention in vivo (A) on macroscopically visible metastasis in nude mice 4 months following transplantation with A375 cells by the intra-cardiac route (B) on survival by Kaplan Meier analysis.

Administration of monoclonal antibodies of the present invention resulted in metastasis inhibition (see FIG. 15A) and survival advantage (see FIG. 15B). As seen in FIGS. 15(A) and (B), there is provided the effect of monoclonal antibodies of the present invention in vivo on metastasis (macroscopic) in nude mice transplanted with A375 cells by the intra-cardiac route (see FIG. 15(A)) and on survival by Kaplan Meier analysis (see FIG. 15(B)). Note the survival advantage of mice treated with either mAbM45 (against PTHrP1-33) or mAbM18 (against PTHrP140-173). 100% of vehicle/control treated animals died within 2 months following tumor cells implantation whereas over 30% of animals treated with either mAbs of the present invention were still alive at 4 months post tumor cells transplantation (see FIG. 15(B)). Autopsy of animals treated with monoclonal antibodies of the present invention up to 4 months showed macroscopic evidence of metastasis in 30% of M45-treated animals and 18% of M18-treated animals (see FIG. 15(A)). Approximately 15% of animals treated with monoclonal antibodies of the present invention showed no apparent health deterioration for up to 8 months post-tumor transplantation. Discontinuation of antibody therapy (4 months after tumor cells implantation) in this group resulted in recurrence of metastatic spread in 50% of animals injected with mAbM45 whereas 0% of animals injected with mAbM18 showed no sign of disease and no evidence of metastatic spread at autopsy in animals injected into the left cardiac ventricle (see FIG. 16). FIG. 16 is a table representing the recurrence of metastatic spread after discontinuation of monoclonal antibodies of the present invention in animals injected with A375 cells into the left cardiac ventricle.

These results show that monoclonal antibodies of the present invention are useful for treating melanoma and its metastatic complications. Furthermore, the therapeutic efficacy of the monoclonal antibody against hPTHrP140-173 was at least equivalent to the monoclonal antibody directed against hPTHrP1-33 indicating that inhibition of the PTHrP isoform 1-173 can be sufficient to obtain the desired effect.

The in vitro efficacy of monoclonal antibodies of the present invention on cell growth and invasion of A375 cells were also demonstrated (see FIG. 12). The monoclonal antibodies mAbM45 and mAbM18 showed the strongest inhibition on cell growth with complete inhibition noted over the time course examined. The monoclonal antibodies mAb158, mAb104 and mAb6 reduced cell growth by approximately 60% as compared to controls (see FIG. 12(B)). All mAbs of the present invention tested reduced invasion through Matrigel by over 50% (see FIG. 12(C)).

Example 3

Mouse Model of Human Metastatic Breast Cancer

Figure 17:
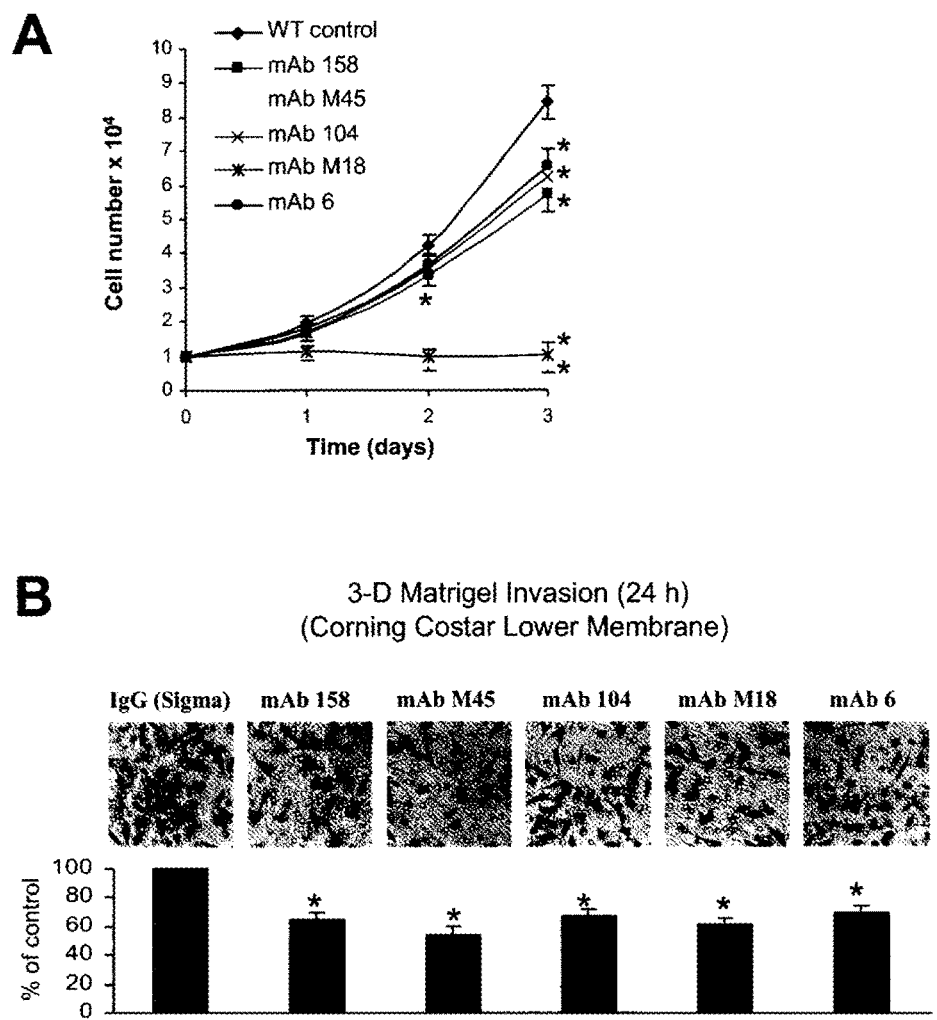
FIGS. 17(A) & (B) show the effect of the neutralizing activity of monoclonal antibodies of the present invention on cell growth and invasion of MDA-MB435 human breast cancer cells. The asterisk (*) indicates a statistically significant difference on cell growth and invasion between MDA-MB-435 cells treated with vehicle control and cells treated with the various mAbs (p≤0.01).

Breast cancer is the most frequent cancer in women (CDC Press Office (2003)). There are several types of breast cancer (Harris J R et al. Diseases of the breast third edition Philadelphia Pa. Lippincott/Williams & Wilkins (2004) p 971)), the most common one arising from mammary epithelial cells (MEC). PTHrP is detected by immunoreactivity in the majority of breast tumors resected at surgery (Southby J et al Cancer Res (1990) 50, 7710). However detection of PTHrP in the blood with immunoassays specific for the N-terminal (including amino acids 1 to 34) or the mid-region (including amino acids 37 to 106) only detected the molecule in advanced stages of breast cancer associated with hypercalcemia but not in the blood of patients without hypercalcemia (Grill V et al J Clin Endocrinol Metab (1991) 73, 1309; Bundred N J et al (1991) Br Med J 303, 1506). In vitro inhibition of PTHrP using siRNA or monoclonal antibodies resulted in both growth inhibition and inhibition of invasion (see FIGS. 17(A) & (B)). As seen in FIG. 17, there is a provided effect of the neutralizing activity of the monoclonal antibodies of the present invention on cell growth (see FIG. 17(A)) and invasion of MDA-MB-435 human breast cancer cells (see FIG. 17(B)). Note the strong inhibitory effect of mAbM45 and mAbM18 on cell growth ($p \leq 0.01$). No statistically significant difference was seen between monoclonal antibodies of the specific subclass (IgG or IgM) directed at the C-terminal end and N-terminal antibodies. Note the complete inhibition of cell growth with the IgM isotype mAbs directed either against the N-terminal (mAbM45) or the C-terminal (mAbM18) end of PTHrP. The IgG isotype mAbs directed against either PTHrP1-33 (mAb158), PTHrP140-173 (mAb104) or PTHrP151-169 (mAb6) had a lesser but similar growth inhibitory effect of about 30% as compared to controls (see FIG. 17(A)). However, all mAbs displayed similar inhibitory effect on invasion, as shown in FIG. 17(B). Antibodies specifically recognizing PTHrP1-173 but not recognizing the other isoforms strongly inhibit growth and invasion of human breast cancer cells. No effect on cell growth or cytotoxic effect was observed in primary normal human mammary epithelial cells treated with the monoclonal antibodies.

Figure 18:
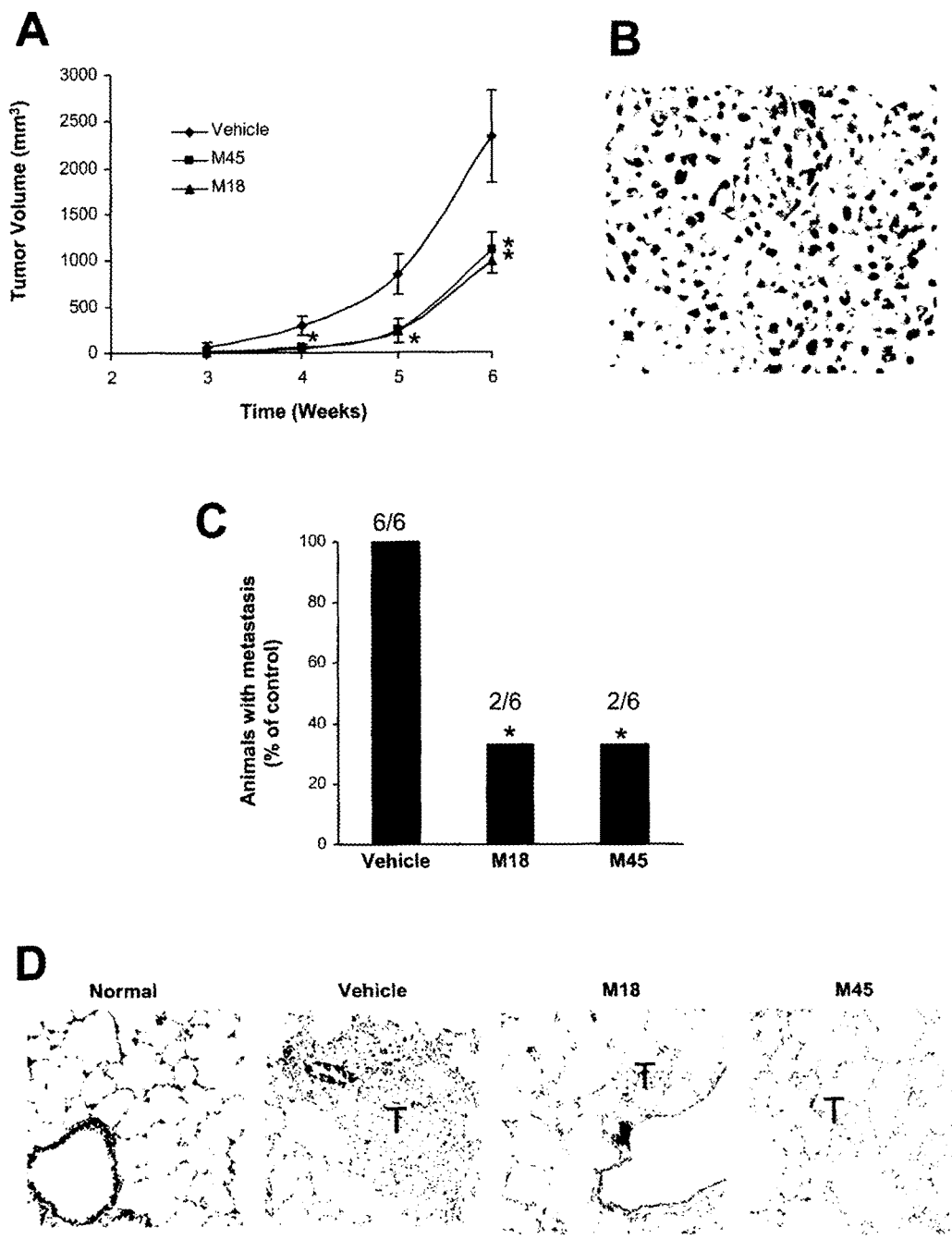
FIGS. 18(A) to (D) show the effect of monoclonal antibodies of the present invention in vivo in nude mice transplanted with the human breast cancer cell line MDA-MB-435 on tumor growth (A) and lung metastases ((C) & (D)). (B) H&E staining of an excised breast tumor. The asterisk (*) indicates a statistically significant difference between animals treated with vehicle control and animals treated with either mAb M45 or M18 on tumor growth and metastasis (p≤0.01).

In the present invention, the monoclonal antibody specific for the C-terminal of the isoform PTHrP1-173 (M18) or directed against all isoforms (M45) were used in nude mice transplanted with the human breast cancer cell line MDA-MB-435 (FIGS. 18(A) to (D) and demonstrated growth inhibition and metastatic spread of breast cancer. FIGS. 18(A), (C) & (D) provide the effect of the monoclonal antibodies in vivo in nude mice transplanted with the human breast cancer cell line MDA-MB-435 on tumor growth and lung metastases. (A) Tumor volume. (B) Hematoxylin and eosin ("H&E") staining of a tumor excised at sacrifice. (C) Percentage of animals with lung metastasis at sacrifice. (D) H&E staining of lungs of vehicle treated animals and animals treated with the mAbs. A normal lung is shown for comparison. T indicates tumor (metastasis) location.

The human breast cancer cell line MDA-MB-435 was transplanted into the mammary fat pad of nude mice and the therapeutic efficacy of the monoclonal antibodies examined on tumor growth and metastasis. When these tumor cells are transplanted into the mammary fat pad, tumor growth and metastasis to lungs can be examined. Tumor growth in untreated animals reaches 1.5-2.0 cm$^3$ approximately 6 weeks post tumor transplantation. At this stage >80% of animals develop lung metastases. In this example, therapeutic efficacy of the monoclonal antibodies mAbM45 and mAbM18 was tested in 4-5 week old female athymic nude mice (BALB/C-nu/nu, Charles River). $1 \times 10^6$ MDA-MB-435 cells suspended in 100 µl of PBS were inoculated into the surgically exposed right flank mammary fat pad under direct vision through a dissecting microscope. Treatment was initiated 1 day after cell inoculation using 100 µg of antibodies injected subcutaneously every two days for 6 weeks. Control animals were injected with 100 µg of non-immune IgM or supernatant of hybridomas from non-immunized animals. The rate of primary tumor growth was determined by plotting the means of two orthogonal diameters of the tumor measured at 5 day intervals.

Administration of monoclonal antibodies of the present invention resulted in a significant reduction of tumor growth (see FIG. 18(A)) and lung metastasis inhibition (see FIGS. 18(C) & (D)). Tumor growth was inhibited by approximately 50% with either the mAb PTHrP1-33 (mAbM45) or PTHrP140-173 (mAbM18) as compared to control animals (see FIG. 18(A)). Furthermore, there was approximately a 70% reduction in the number of animals positively identified with lung metastasis at sacrifice in animals treated with mAbs of the present invention (see FIG. 18(C)). The size of metastasis was also significantly reduced in animals treated with either mAb (see FIG. 10(D)). FIG. 10(B) shows the typical histology of an excised tumor at autopsy. These results show that the monoclonal antibodies of the present invention are useful for treating breast cancer and its metastatic complications. The therapeutic efficacy of the monoclonal antibody against PTHrP 140-173 was equivalent to the monoclonal antibody directed against PTHrP 1-33 indicating that inhibition of the PTHrP isoform 1-173 is sufficient to obtain the desired effect.

Example 4

In Vitro Model for Prostate Cancer

Figure 19:
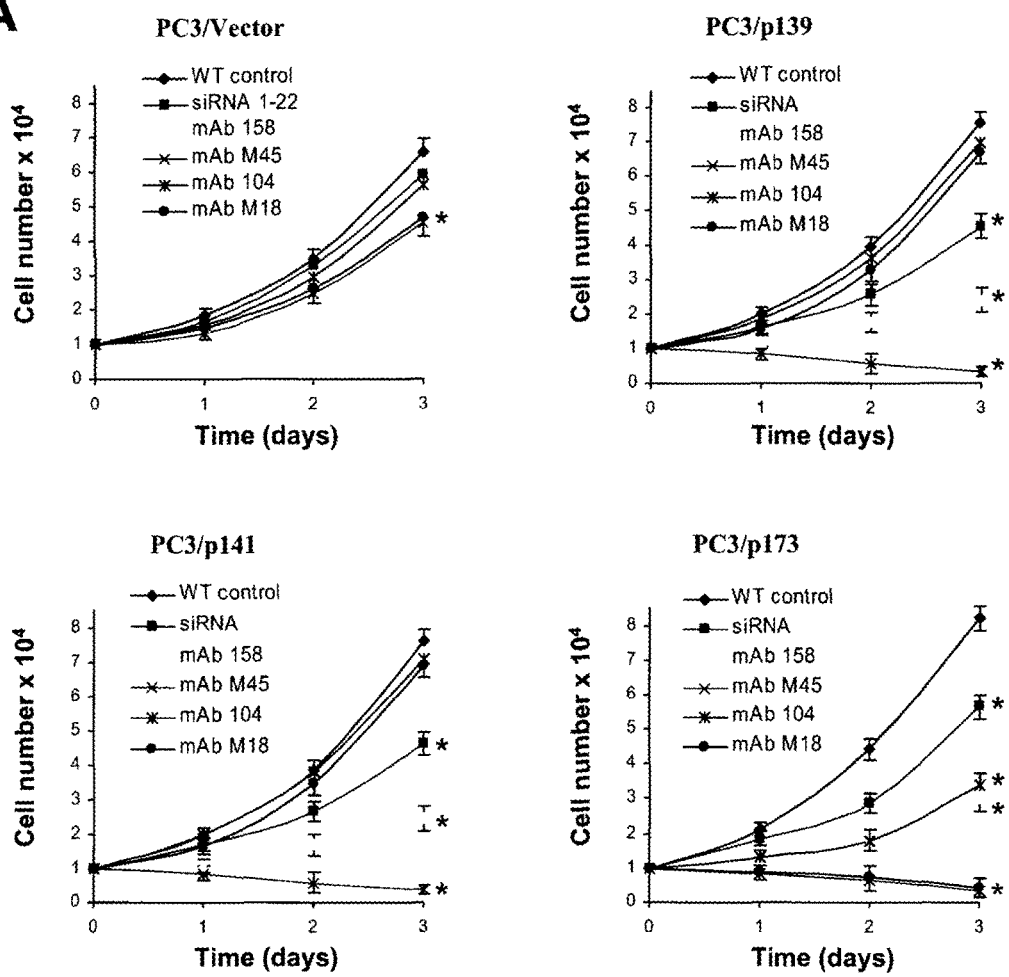
FIGS. 19(A) to (D) show the effect of the neutralizing activity of monoclonal antibodies of the present invention and siRNA on cell growth (A) and invasion ((B), (C), (D)) of PC-3 prostate cancer cells overexpressing the various PTHrP isoforms. The asterisk (*) indicates a statistically significant difference between PC-3 cells treated with vehicle control (WT control) and PC-3 cells treated with the indicated mAbs or with siRNA1-22 on cell growth and invasion (p≤0.01).
Figure 19:
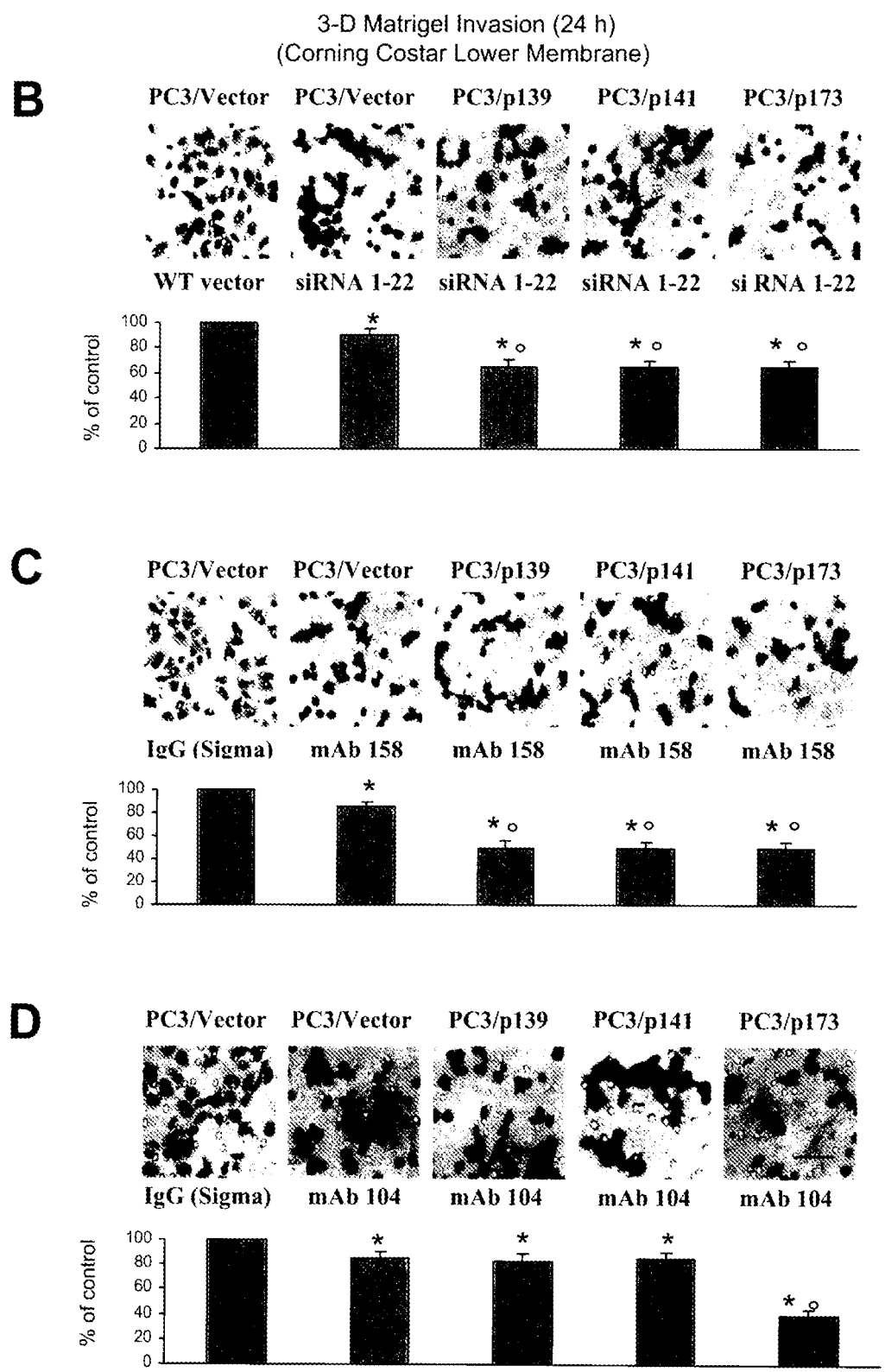

Prostate cancer is the most common type of cancer in men (CDC press office (2003)). It frequently spreads to bone where osteoblastic lesions develop in contrast to osteolytic lesions seen in breast cancer (Roodman D. N Engl J Med (2004) 350, 1655). PTHrP is expressed in the majority of prostate cancer tissues (Deftos L J Cancer (2000) 88, 3002) but its role in prostate cancer in progression and metastasis is unknown. The present invention is directed to knocked down PTHrP in vitro using siRNA technology in two human prostate cancer cell lines and demonstrated a strong inhibition of cell growth and invasion (FIGS. 19(A) to (D)). FIG. 19 shows a graph representing the effect of the neutralizing activity of the monoclonal antibodies (mAb158, mAbM45, mAb104 and mAbM18) and siRNA on cell growth and invasion of PC-3 cells overexpressing the various PTHrP isoforms. Shown in FIG. 19(A) is the effect of the various monoclonal antibodies and siRNA of the present invention on cell growth of the cell lines transfected with vector alone or vector containing specific isoforms. FIGS. 19(B), (C) and (D) show the effect of mAb158 and mAb104 or siRNA on invasion through matrigel. In PC-3 cells transfected with vector alone a moderate inhibition of growth (25%) was achieved with either IgM mAbs directed at PTHrP140-173 (mAbM18) or PTHrP1-33 (mAbM45). A strong inhibitory effect on cell growth was observed in the cell lines overexpressing any of the isoforms (PC3/p139, PC3/p141, PC3/p173) when treated with the mAb directed at the N-terminal end (mAb158 & mAbM45). In contrast, the mAbs directed against PTHrP140-173 (mAb104 & mAbM18) were only effective in the cell line overexpressing PTHrP1-173 (PC-3/p173). SiRNA knockdown of all isoforms using siRNA1-22 was equally effective in all cell lines overexpressing any of the isoforms reducing cell growth by approximately 40%. Furthermore mAbs directed at the C-terminal region of PTHrP (mAb104 and mAbM18) reproduced all the effects of PTHrP inhibition seen with siRNA (siRNA1-22) and similar to the effect observed with the N-terminal antibody against PTHrP (mAb158 and mAbM45) (see FIGS. 19(B) to (E)).

Example 5

In Vitro Model for Squamous Skin Cancer

Skin cancer is the most common form of cancer in the United States. More than 1 million skin cancers are diagnosed annually (National Cancer Institute (2007) SEER database). Squamous cell carcinoma is the second most common form of skin cancer with more than 250,000 cases diagnosed each year in the United States (Christenson L J et al JAMA (2005) 294, 681). Squamous cancer of the skin in humans arises from the transformation of normal human keratinocytes. A well known model of tumor progression was used in which normal human keratinocytes are immortalized with human papilloma virus 16 ("HPV16") to give rise to the non-tumorigenic HPK1A cell line and subsequently transformed into cancer cells by overexpression of an activated H-Ras oncogene to give rise to HPK1Aras cells that develop into a classical squamous tumor. There has been demonstrated a stepwise increase in production of PTHrP associated with malignant transformation in the keratinocyte model of tumor progression.

This tumor progression model in keratinocytes was used to analyze the consequences of PTHrP overexpression in HPV16 HPK1A immortalized cells. HPK1A cells were grown in Dulbecco's modified Eagle's medium (DMEM) supplemented with 10% fetal bovine serum (10% FBS). Sub confluent cells (70%) were transfected overnight with 2 micrograms of an expression vector coding for either the amino acid sequence of the isoforms PTHrP1-139, 1-141 or 1-173 or with a control empty vector (pcDNA3).

Figure 20:
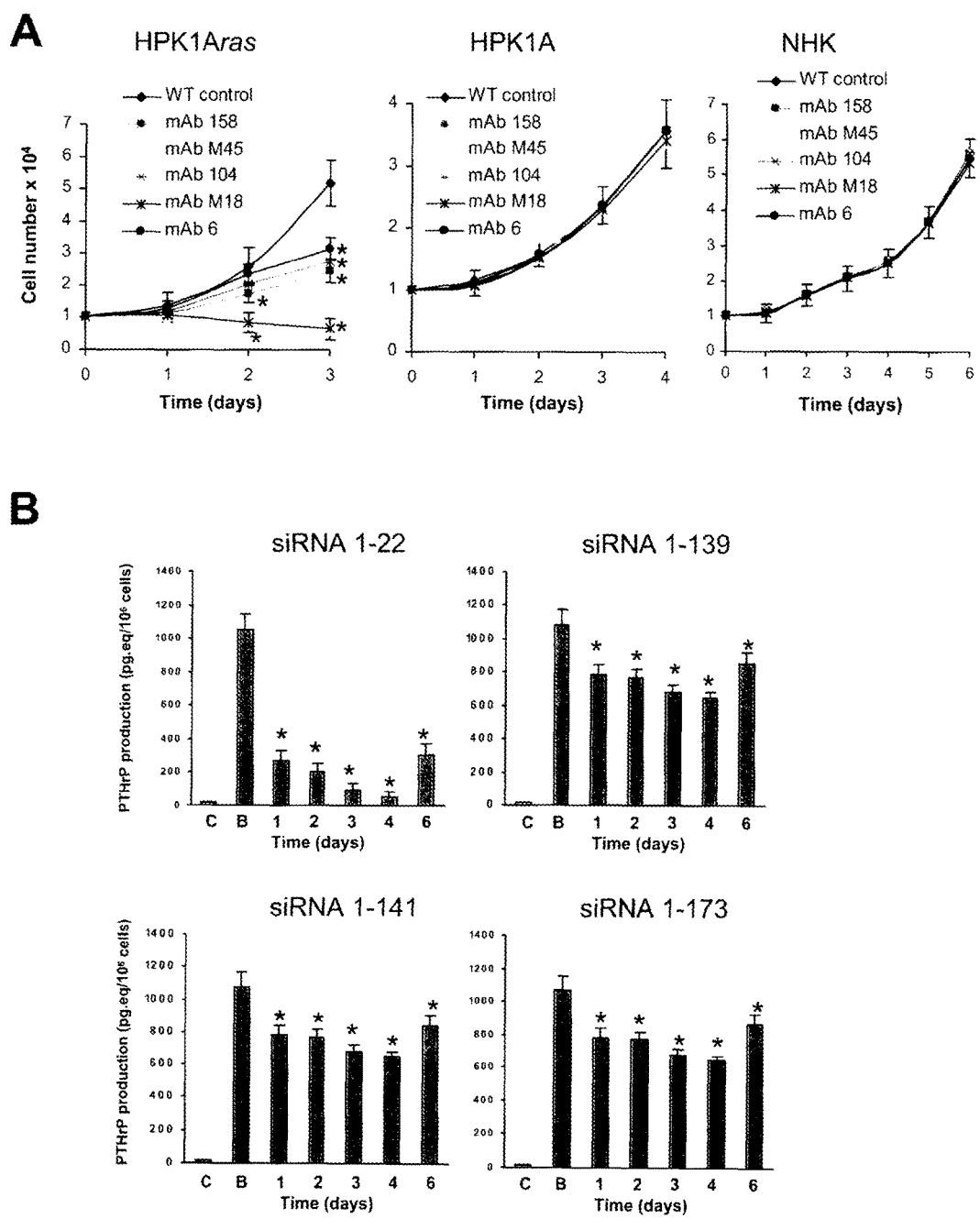
FIGS. 20(A) & (B) show the effect of the neutralizing activity of monoclonal antibodies of the present invention (A) and siRNA specific against each PTHrP isoform (B) of the present invention on cell growth of HPK1Aras cells and in control HPK1A immortalized keratinocytes and normal human keratinocytes (NHK). The asterisk (*) indicates a statistically significant difference between HPK1Aras cells treated with vehicle control (WT control) and HPK1Aras cells treated with various mAbs or between HPK1Aras cells treated with control siRNA and HPK1Aras cells treated with specific siRNAs (p≤0.01).

The in vitro efficacy of the monoclonal antibodies of the present invention on cell growth was demonstrated in the HPK1Aras cell line with a complete inhibition (and evidence of cytotoxicity) and similar efficacy observed with either the N-terminal (mAbM45) or C-terminal (mAbM18) of the IgM subclass. MAbs of the IgG subclass against hPTHrP1-33 (mAb158), hPTHrP 140-173 (mAb 104) and hPTHrP 151-169 (mAb6) inhibited cell growth by approximately 40% without evidence of cytotoxicity (see FIG. 20(A) left panel). FIG. 20(A) (right panel) shows a graph representing the effect of the neutralizing activity of the mAbs specific against the various isoforms on cell growth of the non-tumorigenic immortalized HPK1A cell line and primary normal human keratinocytes (NHK) (Clonetics, CA). No inhibitory effect of the mAbs on cell growth (or evidence of cytotoxicity) was seen with the parent cell line (HPK1A) or with NHK.

FIG. 20(B) shows the effect of siRNA of the present invention against specific PTHrP isoforms on PTHrP production. SiRNA directed against all isoforms (siRNA1-22) inhibits PTHrP production by over 90% at 4 days and that siRNA directed specifically against each isoform PTHrP-139 (siRNA1-139), PTHrP1-141 (siRNA1-141) and PTHrP1-173 (siRNA1-173) inhibits PTHrP by about 30%. Each isoform is also subject to siRNA knock down as seen in FIG. 20(B), namely PTHrP-139 (siRNA1-139), PTHrP1-141 (siRNA1-141) and PTHrP1-173 (siRNA1-173). As can be seen in FIG. 20(B), the cumulative effect of siRNA inhibition of each isoform (siRNA1-139+siRNA1-141+siRNA1-173) is approximately equivalent to the effect of the total inhibition using siRNA1-22, which recognizes all isoforms.

SiRNA Constructs

SiRNA1-22: To inhibit total PTHrP via siRNA through knock down experimentation, the sequences selected for sense and antisense strands of PTHrP, were as follows: sense 5'-CACCA GCT GTG TCT GAA CAT CAG CTC C TTC AAG AGA G GAG CTG ATG TTC AGA CAC AGC-3' (SEQ ID NO: 1); antisense 5'-AAAA GCT GTG TCT GAA CAT CAG CTC C TCT CTT GAA G GAG CTG ATG TTC AGA CAC AGC T-3'(SEQ ID NO: 2). This oligonucleotide sequence was derived based on the sequence of the N-terminal region of hPTHrP amino acid residues 1 to 7 (Ala Val Ser Glu His Gln Leu) (SEQ ID NO: 3).

SiRNA1-139: To inhibit the PTHrP 1-139 isoform, the sequences selected for sense and antisense strands of PTHrP, were as follows: sense 5'-CACCA TAA CAG GCT TCT CTG GCC CGT A TTC AAG AGA T ACG GGC CAG AGA AGC CTG TTA-3' (SEQ ID NO: 4); antisense 5'-AAAA TAA CAG GCT TCT CTG GCC CGT A TCT CTT GAA T ACG GGC CAG AGA AGC CTG TTA T-3' (SEQ ID NO: 5). This oligonucleotide sequence was derived based on the sequence of the 3' untranslated end of hPTHrP 1-139 (5'-CACCA TAA CAG GCT TCT CTG GCC CGT A) (SEQ ID NO: 6) in exon VII.

SiRNA1-141: To inhibit the PTHrP 1-141 isoform, the sequences selected for sense and antisense strands of PTHrP, were as follows: sense 5'-CACCA AGG CAT TGA AAT TTT CAG CAG A TTC AAG AGA T CTG CTG AAA ATT TCA ATG CCT-3' (SEQ ID NO: 7); antisense 5'-AAAA AGG CAT TGA AAT TTT CAG CAG A TCT CTT GAA T CTG CTG AAA ATT TCA ATG CCT T-3' (SEQ ID NO: 8). This oligonucleotide sequence was derived based on amino acids 140-141 (Arg His) and the sequence of the 3' untranslated end of hPTHrP 1-141 (5'-CACCA AGG CAT TGA AAT TTT CAG CAG A) (SEQ ID NO: 9) in exon IX.

SiRNA1-173: To inhibit the PTHrP 1-173 isoform, the sequences selected for sense and antisense strands of PTHrP, were as follows: sense 5'-CACCA ACA GCA CTT CTG TGG GGT TTG A TTC AAG AGA T CAA ACC CCA CAG AAG TGC TGT-3' (SEQ ID NO: 10); antisense 5'-AAAA ACA GCA CTT CTG TGG GGT TTG A TCT CTT GAA T CAA ACC CCA CAG AAG TGC TGT T-3'(SEQ ID NO: 11). This oligonucleotide sequence was derived based on the sequence of the C-terminal region of hPTHrP1-173 (amino acids 140-146 Thr Ala Leu Leu Trp Gly Leu) (SEQ ID NO: 12).

SiRNA1-173: To inhibit the PTHrP 1-173 isoform, the sequences selected for sense and antisense strands of PTHrP, were as follows: sense 5'-CACCA ACA GCA CTT CTG TGG GGT TTG A TTC AAG AGA T CAA ACC CCA CAG AAG TGC TGT-3'; antisense 5'-AAAA ACA GCA CTT CTG TGG GGT TTG A TCT CTT GAA T CAA ACC CCA CAG AAG TGC TGT T-3'. This oligonucleotide sequence was derived based on the sequence of the C-terminal region of hPTHrP1-173 (amino acids 140-146 Thr Ala Leu Leu Trp Gly Leu)

The oligonucleotide sequences in the siRNA constructs of the present invention have no homology to any gene sequence obtained with GenBank data using the BLAST program (GenBank). Synthetic oligonucleotides of the above noted sequences were synthesized by Invitrogen life Technologies (Burlington, ON) and annealed to generate a short double-stranded oligonucleotide and cloned into the pENTR™/H1/TO vector using a BLOCK-iT™ inducible H1 RNAi Entry Vector Kit (Invitrogen life Technologies, Burlington, ON) according to the manufacturer's specifications. Anti-hPTHrP siRNA constructs were sequenced before use (Sheldon Biotechnology Centre, McGill University, Montreal, Canada). Cells were transiently transfected overnight with 2 ug of the anti-PTHrP siRNA plasmid construct or with pENTR™/H1/TO vector alone using 10 ul of LipofectAMINE (Gibco BRL, Burlington, ON, Canada) in serum-free DMEM. The medium was then replaced with DMEM supplemented with 10% FBS. Cell growth and invasion of the transfected A375, PC-3 and HPK1Aras cells was then assessed (see FIGS. 13, 19 & 20)

PTHrP Expression

The PTHrP expression vectors of the present invention were constructed as follows.

Poly (A)⁺ mRNA was isolated with the Quick Prep Micro mRNA purification kit according to the manufacturer's protocol (Amersham Pharmacia Biotech, Baie d'Urfe, QC, Canada). After precipitation, the mRNA was dissolved in DEPC treated water and subjected to DNAse I treatment. 2 µg of poly(A)⁺ mRNA isolated from cell was used as a template for first strand synthesis by the random primer method using reverse transcriptase, Superscript™ RT (200 U/µl) (GIBCO BRL, Burlington, ON) in the presence of 1 mM of each dNTP, 20 units of RNAse inhibitor (Amersham Pharmacia Biotech, Baie d'Urfe, Qc, Canada).) and 1× reaction buffer for 2 h at 37° C. cDNAs were then amplified by PCR (30 cycles of 92° C., 1 min; 55° C., 1 min; 72° C., 1 min) using HOT TUB DNA polymerase (3.0 U/µl) (Amersham Pharmacia Biotech, Baie d'Urfe, Qc, Canada) in the presence of 1 mM of each dNTP, 2.5 mM MgCl2, 1× reaction buffer and 500 ng of primer. The following oligonucleotide primers (Sheldon Biotechnology Center at McGill University, Montreal) were used to amplify 546, 550 and 846 bp cDNA fragment corresponding to the 3 isoforms of human PTHrP cDNA as noted herein (see FIG. 3(A)):

```
                                      (SEQ ID NO: 13)
forward N-38: 5' AGACGATGCAGCGGAGACTGGTTCA 3';

(SEQ ID NO: 14)
reverse C139: 5' CCAGAGAAGCCTGTTACCGTGAATCG 3';

(SEQ ID NO: 15)
reverse C141: 5' GGTCTCTGCTGAAAATTTCAATGCC 3';
and (SEQ ID NO: 16)
reverse C173: 5' GCAGGATAGGTCATTCACTGTGCTC 3'.
```

The following oligonucleotide primers were used to amplify a 1780 bp cDNA fragment corresponding to human PTH/PTHrP type 1 receptor cDNA based on its published sequence.

(i) forward PRIN: 5' ATGGGGACCGCCCGGATC 3' (SEQ ID NO: 17); and (ii) reverse PRIC: 5' TCACATGACTGTCTCCCACTC 3' (SEQ ID NO: 18).

RT-PCR products were analyzed on a 1.5% agarose gel, using 1 kb DNA (GIBCO BRL, Burlington, ON) as the molecular weight marker. Nucleotide sequence of the PCR products was determined with automatic sequencing (Sheldon Biotechnology Center at McGill University, Montreal).

The PCR products were then cloned into the pCRII vector using a TA cloning kit (Invitrogen life Technologies, Burlington, ON). All three PTHrP cDNA isoforms were then inserted into the EcoRI restriction endonuclease site of pcDNA3 expression vector (Invitrogen life Technologies, Burlington, ON) in order to be expressed by CMV promoter and their sequences subjected to sequencing were found identical to human published PTHrP cDNA sequences (Yasuda et al 1988 and GenBank data library J04710).

The PTHrP1-173 encoding sequence was also fused with green fluorescent protein (GFP) using EcoRI/BamHI restriction endonuclease sites in pEGFP-N1 vector (Clontech Laboratories Inc, Mountain View, Calif.) for the purpose of in vitro and in vivo detection of the protein product expression in tumor cells using fluorescence detection or imaging. The GFP is cloned downstream of PTHrP and therefore co-expressed in the cells that may express the particular PTHrP isoform.

The HPK1A cells that were stably transfected with the pcDNA3 expression vector containing the cDNA for the PTHrP 1-173 isoform are hereby referred to as HPK1A/p173. The HPK1A cells that were stably transfected with the pcDNA3 expression vector containing the cDNA for the PTHrP 1-141 isoform are hereby referred to as HPK1A/p141. The HPK1A cells that were stably transfected with the pcDNA3 expression vector containing the cDNA for the PTHrP 1-139 isoform are hereby referred to as HPK1A/p139.

In the stably transfected cells HPK1A/p173, HPK1A/p141, HPK1A/p139, it was demonstrated the changes in morphology of HPV16 immortalized cells following overexpression of the various isoforms. FIGS. 1(A) to 1(C) show the effect of overexpression of the PTHRP1-141 and 1-173 isoforms in HPK1A cells on cell growth (FIG. 1(A)), on cell morphology (FIG. 1(B)) and on growth in soft agar (FIG. 1(C)). Overexpression of the PTHrP 1-173 isoform in the HPK1A/p173 resulted in these cells being elongated and growing in multiple layers (see FIG. 1(B)). There was an increase in growth velocity, cell morphology and anchorage independent growth in cells transfected with PTHrP1-173 (HPK1A/p173) (p≤0.01). Also shown in FIGS. 1(A) to 1(C), overexpression of PTHrP1-141 (HPK1A/p141) or transfection of vector alone (HPK1A/Vector) did not affect the morphology of the HPK1A cells which remained identical to wild type HPK1A cells (HPK1A) (see FIG. 1(B)). HPK1A cells overexpressing PTHrP1-173 (HPK1A/p173) but neither 1-141 (HPK1A/p141) nor control cells (HPK1A/Vector and wild type HPK1A) formed colonies in soft agar (see FIG. 1(C)).

The cell line HPK1A/p173 was transplanted subcutaneously into nude mice and showed evidence of tumor growth which is not seen with nude mice transplanted with the control HPK1A cell line or HPK1A overexpressing PTHrP1-141 (HPK1A/p141) (see FIGS. 2(A) & 2(B)). FIG. 2(A) is a photograph showing excised subcutaneous lesions in nude mice transplanted with the PTHrP overexpressing cell lines HPK1A/p173 and HPK1A/p141, control HPK1A cell lines (wild type HPK1A and HPK1A expressing vector alone) as well as positive control tumors of mouse transplanted with HPK1Aras cells. As shown in FIG. 2(B), there is provided tumor growth velocity in nude mice transplanted with the same cell lines wherein only HPK1A cells transfected with PTHrP1-173 (HPK1A/P173) developed tumor in nude mice similar to mice transplanted with the malignant cell line HPK1Aras. Mice transplanted with HPK1Aras cells were used as positive controls (see FIG. 2(A)). 5/5(100%) mice transplanted with the HPK1A transformed cell line (HPK1A/p173) or HPK1Aras cells developed tumors within 4 weeks whereas none of the mice transplanted with the parent cell line (HPK1A) developed tumors (the small excised lesions shown were fibrotic with no evidence of tumor cells). Karyotype analysis of the transformed HPK1A/p173 cells confirmed their cellular origin.

In vitro morphology and in vivo behavior of these transformed cells were similar to HPK1A cells transformed with the H-ras oncogene (HPK1Aras) (Rhim J S et al Oncogene (1989)4, 1403) indicating that the overexpression of the PTHrP 1-173 isoform has oncogenic properties. Significantly, only over expression of PTHrP 1-173 but not of the isoform (PTHrP1-141) resulted in cellular transformation in vitro and tumor growth in vivo (see FIGS. 1& 2).

Figure 3:
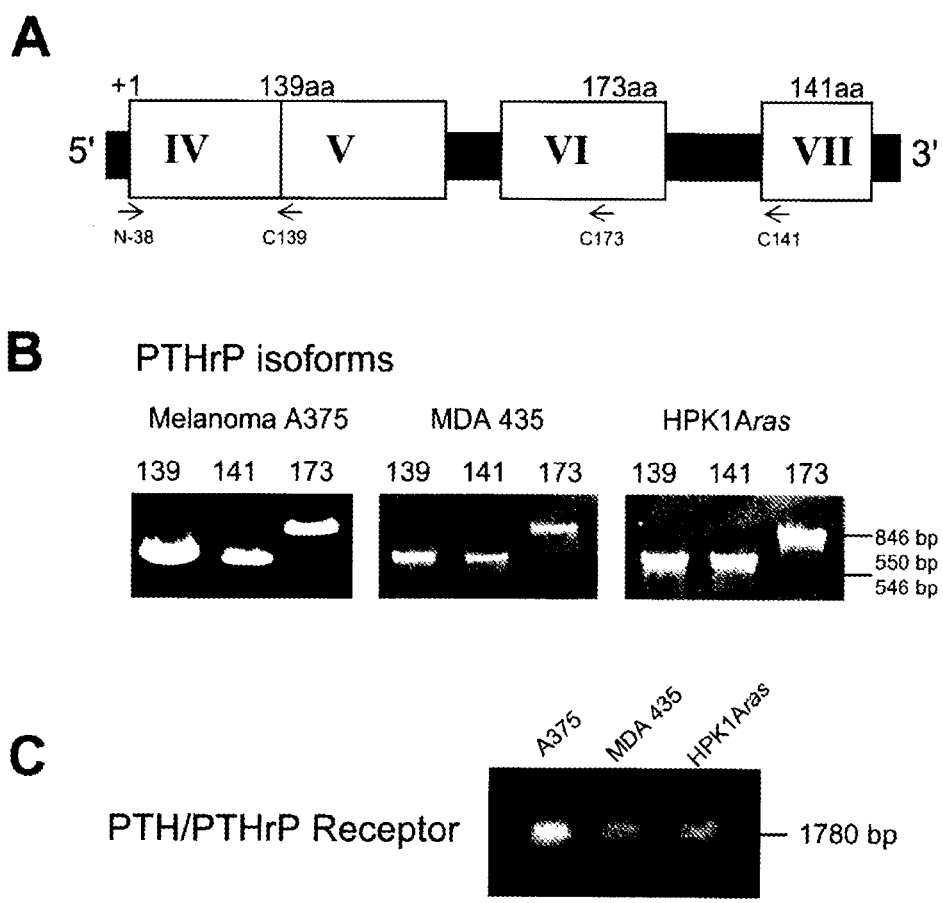
FIGS. 3(A) to (C) show the gene structure of PTHrP (A); the expression of the three isoforms (PTHrP1-139, PTHrP1-141 and PTHrP1-173) by RT-PCR in HPK1Aras, A375 and MDA-MB-435 human cancer cell lines (B) and the presence of the PTH/PTHrP receptor (C).

The three isoforms were shown to be expressed in the transformed HPK1Aras cell line as well as other human malignant cell lines as demonstrated by RT-PCR (FIG. 3(A) to 3(D)). As seen in FIG. 3, there is shown the expression of the three isoforms (PTHrP1-139, PTHrP1-141, PTHrP1-173) by RT-PCR in HPK1Aras, A375 and MDA-MB-435 human cancer cell lines. FIG. 3(A) provides the position of the primers used for the RT-PCR while FIG. 3(B) shows the results of the RT-PCR expression of the three isoforms in the cell lines indicated. FIG. 3(C) provides the RT-PCR expression of the PTH/PTHrP type1 receptor. This demonstrates that both the receptor and its ligand(s) are co-expressed in the same cell lines.

Figure 4:
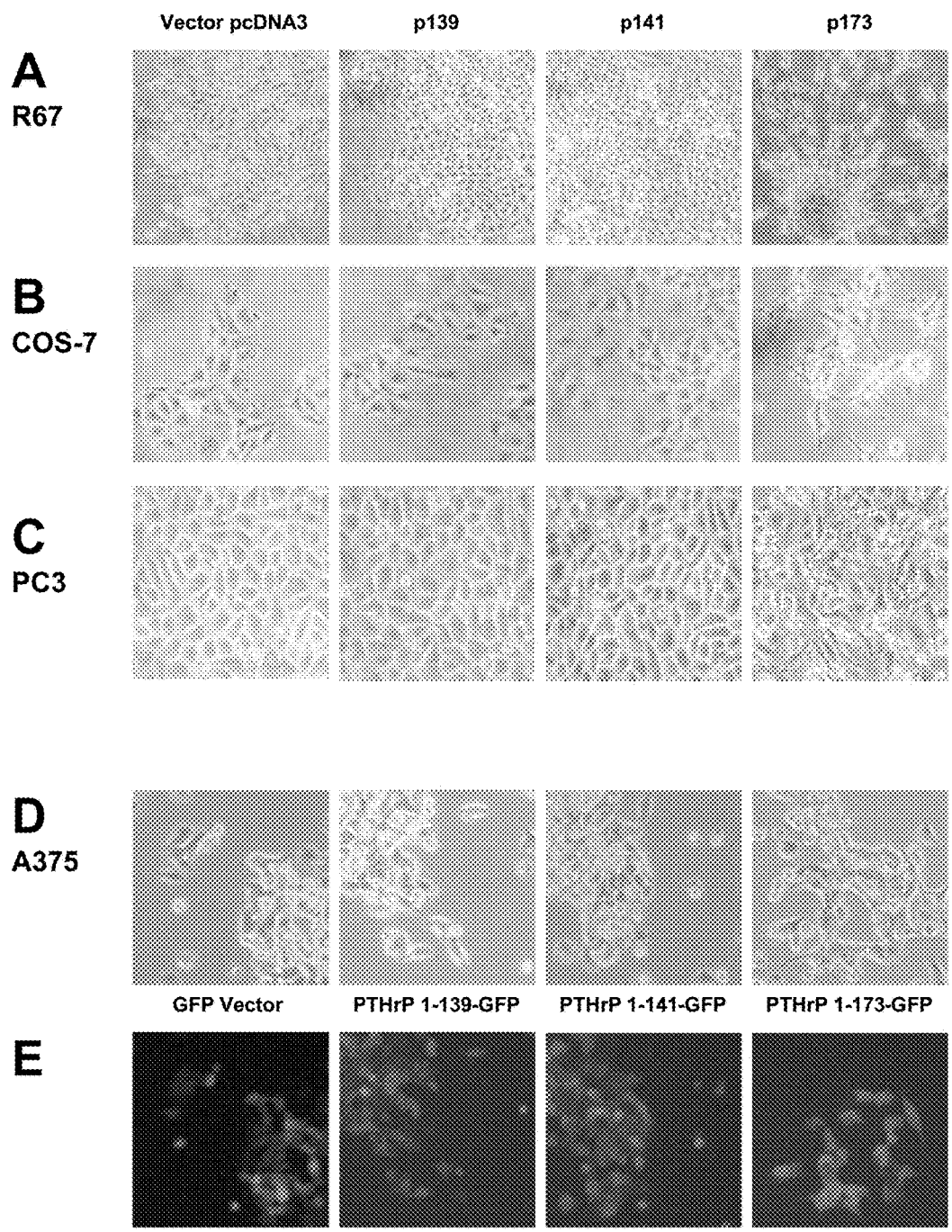
FIGS. 4 (A) to (E) is a photograph showing the effect of PTHrP overexpression of the different isoforms on cell morphology in different cell lines: (A) R-67 immortalized human renal proximal tubular cells; (B) Cos-7 cells; (C) PC-3 human prostate cancer cell line; (D) A375 human melanoma cells; and (E) A375 cells co-expressing GFP and the various isoforms.

As seen in FIGS. 4(A) to (D), there is provided the effect on cell morphology of PTHrP isoforms overexpression in other cell lines including the prostate cancer cell line PC3, Cos7-cells, A375 human melanoma cells and the immortalized human proximal tubular cell line R67. FIG. 4(A) provides R67 immortalized human renal proximal tubular cells. FIG. 4(B) provides African green monkey kidney cells transformed with SV40A (Cos-7 cells). FIG. 4(C) provides PC-3 human prostate cancer cells. FIG. 4(D) provides A375 human melanoma cells. Lower panel shows A375 cells co-expressing GFP and the various isoforms (See FIG. 4(E)).

As shown in FIGS. 4(A) to (C) only stable overexpression of the PTHrP 1-173 isoform induced morphological changes but not cells transfected with vector alone or either the PTHrP1-139 or 1-141 isoforms. PTHrP1-173 overexpression enhanced in vitro invasion as assessed by the Matrigel assay done as noted herein. Matrigel-coated Costar 24-well transwell cell culture chambers divided with an 8.0 µm pore polyvinylpyrrolidone-free polycarbonate membrane (Corning Inc. Corning, N.Y.) were used. These chambers have been shown previously to permit invasion of human melanoma cells. The chamber membrane was coated with a mixture of matrigel basement membrane components (Matrigel, 30 µg/ml) (Becton Dickinson Labware, Bedford, Mass.), incubated for 48 h at room temperature in a laminar flow and UV hood, and stored at 4° C. The coated membrane was rehydrated with 0.2 ml of serum-free DMEM for 2 h. To examine chemotaxis, the rehydration solution was removed and 700 µl DMEM containing 10% FBS was added to each plate well. Cells were trypsinized, washed twice with serum-free DMEM and $5 \times 10^4$ cells resuspended in 0.5 ml serum-free DMEM, deposited onto the upper chamber, and incubated at 37° C. for 24 h, 5% $CO_2$ in a humidified tissue culture incubator. Medium was then removed and cells remaining on the upper side of the membrane were scraped off with a cotton tipped applicator and washed twice with PBS. The invasive cells that migrated to the lower side, and those growing on the under surface of the membrane were fixed with a solution containing 0.5% glutaraldehyde, 2% paraformaldehyde and 0.1M phosphate buffer pH 7.4 for 30 min, stained with Tol Blue solution, and mounted onto glass slides. Ten random fields per membrane were counted under the microscope (Nikon, Eclipse TE300, Japan; Digital Camera C4742-98, LUDL Electronic Products LTD, Hawthorne, N.Y.) to determine the mean number of invasive cells. Data were expressed as the mean (±SEM) number of cells reaching the lower surface of the membrane in three independent experiments (see FIGS. 12, 13 & 17).

Analysis of PTHrP production in the conditioned media collected from different cell lines was done using a PTHrP immunoradiometric assay (DSL-8100, Diagnostic Systems Laboratories, Webster, Tex.) directed against PTHrP 1-86. It has a sensitivity of 0.3 pmol/L (3.0 pg/ml). Conditioned medium were collected at timed intervals, centrifuged to remove debris, and stored at −80° C. until assayed. Non-conditioned DMEM, 10% FBS medium was used as a blank and subtracted from all values. Prior to transfection with the PTHrP isoforms, the cell lines produced variable levels of PTHrP with the highest one seen in A375 cells and the lowest ones seen in PC3 and HPK1A cells. Transfected cells invariably produced high levels of PTHrP as shown in Table 1.

Example 6

Conditional Knock-Out Model

Figure 21:
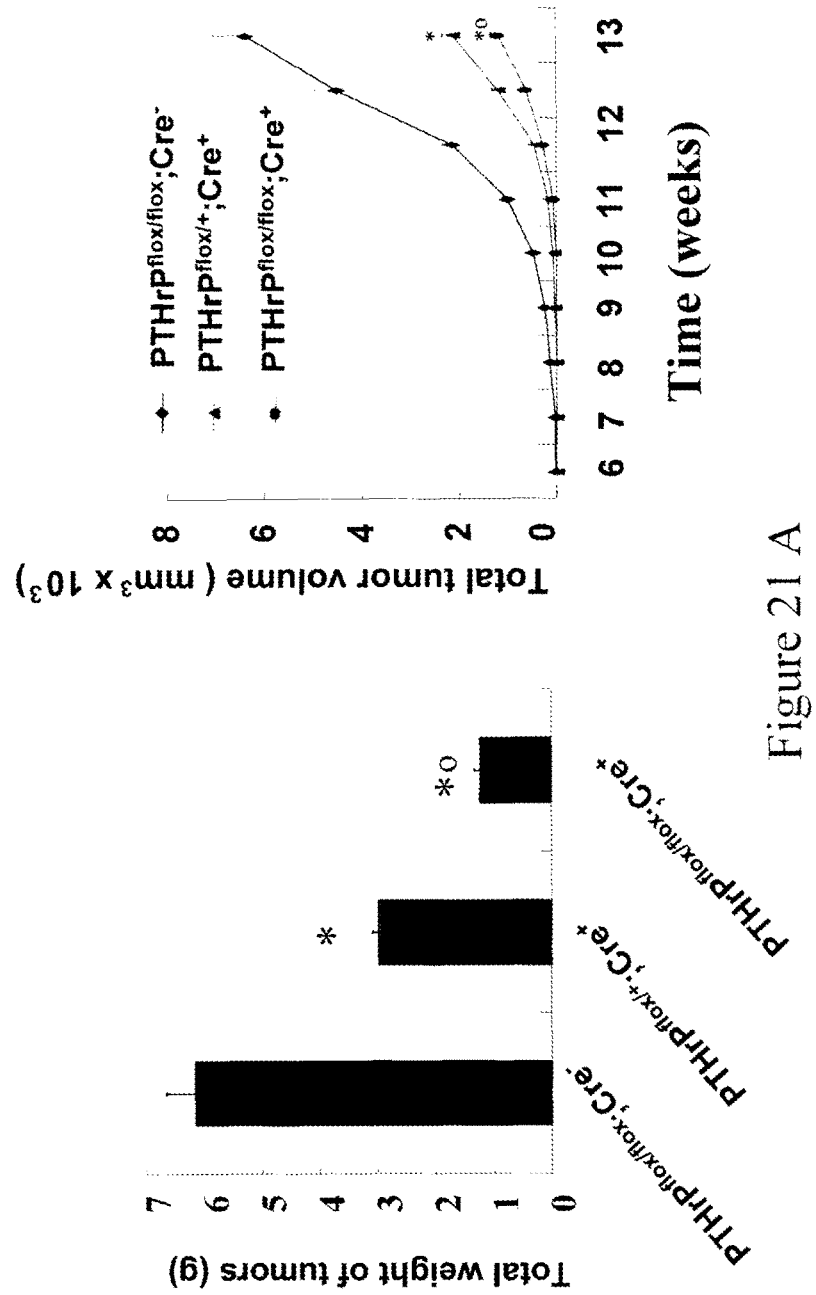
FIGS. 21(A) and B show the results of PTHrP knockout in mammary epithelial cells of the PyVMT mammary tumor progression model:wild type controls (PyVMT-PTHrP$^{flox/flox}$-Cre$^-$ and PyVMT-PTHrP$^{+/+}$-Cre$^+$), heterozygous (PyVMT-PTHrP$^{+/flox}$-Cre$^+$) and homozygous (PyVMT-PTHrP$^{flox/flox}$-Cre$^+$) animals. (A) Tumor growth over time and tumor weight at sacrifice. (B) Kaplan Meeir analysis of tumor onset. The asterisk (*) indicates a statistically significant difference between control PyVMT animals and both homozygous and heterozygous animals and °p≤0.01 indicates a statistically significant difference between homozygous and heterozygous animals (p≤0.01).
Figure 21:
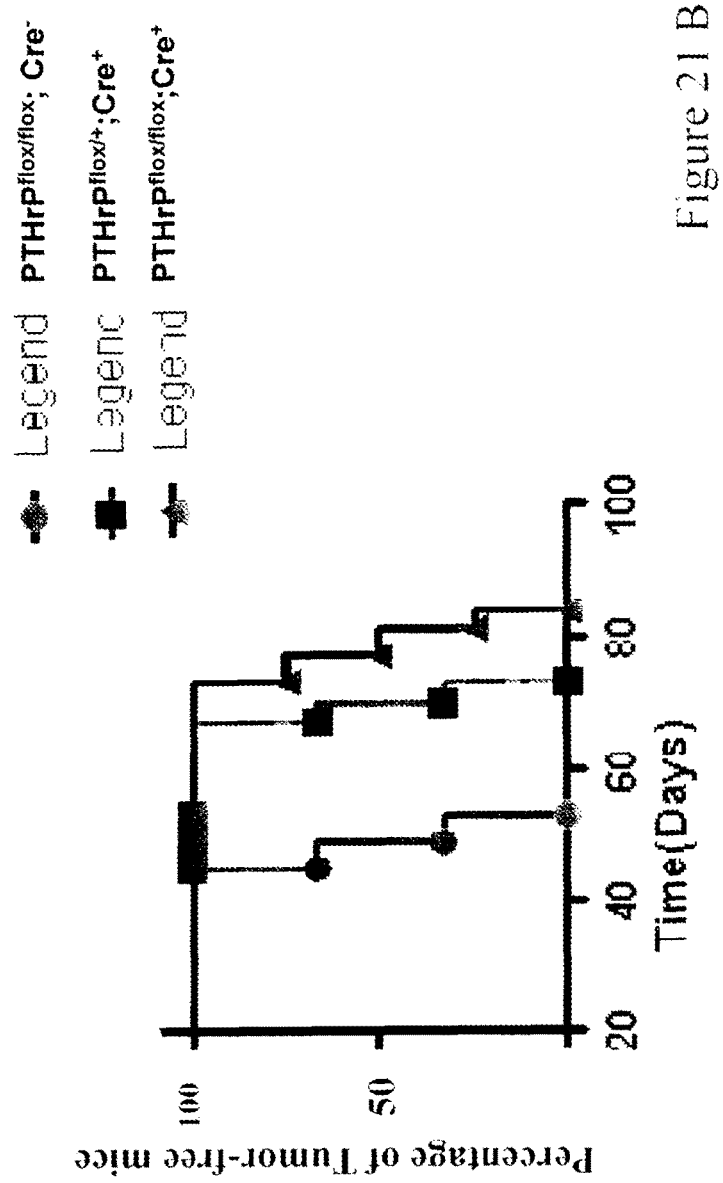

A conditional knock-out model in which the PTHrP gene was specifically ablated in mammary epithelial cells was developed. In this model, the Cre/LoxP recombination system was used to disrupt PTHrP function in the mammary epithelium of a transgenic mouse model of human breast cancer (PyVMT). In this model, hyperplasia occurs at 4-5 weeks, adenocarcinoma at 7-8 weeks and pulmonary metastasis at 12-13 weeks in 100% of animals. Mice carrying a conditional PTHrP allele in which the fourth coding exon was flanked by LoxP recombination sites were backcrossed on an FVB background. These mice were first crossed with the PyVMT mammary tumor model and then with a separate transgenic strain expressing Cre in the mammary epithelium (MMTV/Cre) both on an FVB background. Targeted excision of the PTHrP allele was confirmed using molecular and histological approaches. Ablation of PTHrP in normal FVB animals did not interfere with mammary ductal outgrowth. Ablation of PTHrP in PyVMT animals significantly delayed tumor onset demonstrated by Kaplan Meier analysis (see FIG. 21(A)). At age 50 days, 50% of control animals (PyVMT-PTHrP$^{flox/flox}$-Cre$^−$ and PyVMT-PTHrP$^{+/+}$-Cre$^+$) had a palpable tumor as compared to age 67 days (p<0.005) in heterozygous (PyVMT-PTHrP$^{+/flox}$-Cre$^+$) and 78 days (p<0.001) in homozygous (PyVMT-PTHrP$^{flox/flox}$-Cre$^+$) animals. In addition tumor growth slowed significantly over time with a significant reduction observed in both PyVMT$^{flox/+}$-Cre$^+$ and PyVMT-PTHrP$^{flox/flox}$-Cre$^+$ animals at all time points (FIG. 21). Tumor weight at sacrifice was significantly reduced in homozygous (67±5% p<0.001) and heterozygous animals (48±8% p<0.005) (see FIG. 21). Finally, metastatic spread to lungs at sacrifice was seen in 14/14 control animals, 0/13 homozygous animals and 6/14 heterozygous animals. Molecular and immunohistochemical analysis of tumor tissues revealed an 80% inhibition of markers of tumor progression including cyclin D1, Neu/Erb2 and Ki67 in homozygous PyVMT-PTHrP$^{flox/flox}$-Cre$^+$ animals and a 40% reduction in heterozygous PyVMT-PTHrP$^{flox/+}$-Cre$^+$ animals.

REFERENCES

Bagi C. Skeletal complications of malignancy—Third North American Symposium. IDrugs (2002) 5:553-556.

Birch M A et al. Parathyroid hormone (PTH)/PTH-related protein (PTHrP) receptor expression and mitogenic responses in human breast cancer cell lines. Br J Cancer (1995) 72:90-5.

Bouizar Z et al. Polymerase chain reaction analysis of parathyroid hormone-related protein gene expression in breast cancer patients and occurrence of bone metastases. Cancer Res (1993) 53:5076-8.

Bundred et al. Parathyroid hormone related protein and hypercalcemia in breast cancer. Br Med J (1991) 303:1506-1509.

Budayr A A et al. Increased serum levels of a parathyroid hormone-like protein in malignancy-associated hypercalcemia. Ann Intern Med (1989) 111:807-812.

Campos R V et al. Differential expression of RNA transcripts encoding unique carboxy-terminal sequences of human parathyroid hormone-related peptide. Mol. Endocrinol. (1994) 8:1656-66.

Carron J A et al. PTHrP and the PTH/PTHrP receptor are co-expressed in human breast and colon tumors. Br J Cancer (1997) 76:1095-8.

CDC Press Release. Latest cancer incidence report shows prostate leading cancer among men, breast cancer leads for women. (2003) http://www.cdc.gov/cancer Christenson L J et al. Incidence of basal cell and squamous cell carcinomas in a population younger than 40 years. JAMA (2005) 294:681-690.

Deftos L J. Prostate carcinoma. Production of bioactive factors. Second North American Symposium on Skeletal Complications of Malignancy (1999).

Diel I G et al. Reduction in new metastases in breast cancer with adjuvant clodronate treatment. N Engl J Med (1998) 339:357-363.

Fahn H J et al. The incidence and prognostic significance of humoral hypercalcemia in renal cell carcinoma. J Urol (1991) 145:248-250.

Grill V et al. Parathyroid hormone-related protein: elevated levels in both humoral hypercalcemia of malignancy and in hypercalcemia complicating metastatic breast cancer. J Clin Endocrinol Metab (1991) 73:1309-1315.

Grone A et al. Cloning and sequencing of the 3' region of the canine parathyroid hormone-related protein gene and analysis of alternative mRNA splicing in two canine carcinomas. Domest. Anim. Endocrinol. (2002) 22(3):169-77.

Gallwitz W E et al. Guanosine nucleotides inhibit different syndromes of PTHrP excess caused by human cancers in vivo. J. Clin. Invest. (2002) 110:1559-72.

Guise T A et al. Evidence for a causal role of parathyroid hormone-related protein in the pathogenesis of human breast cancer-mediated osteolysis. J. Clin. Invest. (1996) 98:1544-49.

Hall H I et al. Update on the incidence and mortality from melanoma in the United States. J. Am. Acad. Dermatol. (1999) 40:35-42.

Hanahan D et al. The hallmarks of cancer. Cell (2000) 100:57-70.

Harris J R et al. Diseases of the breast. Third edition. Philadelphia Pa. Lippincot/Williams & Wilkins (2004) p971.

Hortobagyi G N et al. Efficacy of pamidronate in reducing skeletal complications in patients with breast cancer and lytic bone metastases. N Engl J Med (1996) 335:1785-1791.

Insogna K L et al. Native and a synthetic analogue of the malignancy-associated parathyroid hormone-like protein have in vitro transforming growth factor-like properties. J Clin Invest (1989) 83:1057-1060.

Iwamura M et al. Parathyroid hormone-related protein is an independent prognostic factor for renal cell carcinoma. Cancer (1999) 86:1028-1034.

Kao P C et al. Parathyroid hormone-related peptide in plasma of patients with hypercalcemia and malignancy lesions. Mayo Clin Proc (1990) 65:1399-1407.

Kissin M W et al. Parathyroid hormone related protein in breast cancer of widely varying prognostic. Eur J Surg Oncol (1993) 19:134-142.

Kremer R et al. Parathyroid hormone related peptide in hematologic malignancies. Am J Med (1996) 100:406-411.

Kumari R et al. Nuclear targeting of a midregion PTHrP fragment is necessary for stimulating growth in breast cancer cells. Int J Cancer (2006) 119:49-59.

Lauth M et al. Non-melanoma skin cancer: pathogenesis and mechanisms. Drug Discovery Today: Disease Mechanisms (2004) 1:267-72.

Li J et al. Conditional Ablation of Parathyroid Hormone Related Peptide (PTHrP) in Mammary Epithelial Cells Inhibits Breast Cancer Progression. Proceedings of the ASBMR 2007

Liapis H et al. Expression of parathyroidlike protein in normal, proliferative and neoplastic human breast tissues. Am J Pathol (1993) 143:1169-78.

Lichtman S S. Treatment of bone metastases—bisphosphonates and future directions. $34^{th}$ Annual Meeting of the American Society of Clinical Oncology.

Linforth R et al. Coexpression of parathyroid hormone related protein and its receptor in early breast cancer predicts poor patient survival. Clin Cancer Res (2002) 8:3172-3177.

Manenti G et al. A cancer modifier role for parathyroid hormone-related protein. Oncogene (2000) 19:5324-28.

Nishigaki Y et al. Increased serum and urinary levels of a parathyroid hormone-related protein COOH terminus in non-small cell lung cancer patients. Clin Cancer Res (1999) 5:1473-81.

Nishihara M et al. Clinicopathological implications of parathyroid hormone-related protein in human colorectal tumors. J Pathol (1999) 187:217-222.

Percherstorfer M et al. Parathyroid hormone-related protein and life expectancy in hypercalcemic cancer patients. J Clin Endocrinol Metab (1994) 76:1268-1270.

Powell G J et al. Localization of parathyroid hormone-related protein in breast cancer metastases: increased incidence in bone compared with other sites. Cancer Res (1991) 51:3059-3061.

Ralston S et al. Hypercalcaemia and metastatic bone disease: is there a causal link? Lancet (1982) 2:903-905.

Ratcliffe W A et al. Immunoreactivity of plasma parathyrin-related peptide: three region specific radioimmunoassay and a two-site immunoradiometric assay compared. Clin Chem (1991) 37:1781-1787.

Rhim J S et al. Neoplastic transformations of human keratinocytes by polybrene-induced DNA-mediated transfer of an activated oncogene. Oncogene (1989) 4:1403-1409.

Rhim J S et al. Evidence for the multistep value of in vitro human epitheleial cell carcinogenesis. Cancer Res. (1990) 50:5653.

Richard V et al. Quantitative evaluation of alternative promoter usage and 3' splice variants for parathyroid hormone-related protein by real-time reverse transcription-PCR. Clin Chem (2003) 49:1398-1402.

Roodman D. Mechanisms of bone metastasis N. Engl. J. Med. (2004) 350:1655-1664.

Saito H et al. Humanized monoclonal antibody against parathyroid hormone-related protein suppresses osteolytic bone metastasis of human breast cancer cells derived from MDA-MB-231. Anticancer Res (2005) 25:3817-23.

San Miguel J F et al. Prognostic factors and classification in multiple myeloma. Br J Cancer (1989) 59:113-118.

Sato K et al. Treatment of malignancy-associated hypercalcemia and cachexia with humanized anti-parathyroid hormone-related protein antibody. Semin Oncol (2003) 30:167-173.

Sellers R S et al. Alternative splicing of parathyroid hormone-related protein mRNA: expression and stability. J Mol Endocrinol (2004) 33:227-241.

Shen X et al. Increased cell survival, migration invasion, and Akt expression overexpressing LoVo cancer cell lines. Regul. Pept. (2007) January 10; 17276526.

Shen X et al. PTH-related protein enhances LoVo colon cancer cell proliferation, adh integrin expression. Regul. Pept. (2005) 125:17-27.

Shen X et al. PTH-related protein enhances MCF-7 breast cancer cell adhesion, migr invasion via an intracrine pathway. Exp. Cell Res. (2004) 294:420-33.

Shen X et al. PTH-related protein modulates PC-3 prostate cancer cell adhesion an subunit profile. Mol. Cell Endocrinol. (2003) 199:165-77.

Shields J D et al. Lymphatic density and metastatic spread in human malignant melanoma. British Journal of Cancer (2004) 90:693-700.

Southby J et al. Immunohistochemical localization of parathyroid hormone-related protein in human breast cancer. Cancer Res (1990) 50:7710-7716.

Talon I et al. Antitumor effect of parathyroid hormone-related protein neutralizing antibody in human renal cell carcinoma in vitro and in vivo. Carcinogenesis (2006) 27:73-83.

Terkeltaub R et al. Parathyroid hormone-related proteins is abundant in osteoarthritic cartilage, and the parathyroid hormone-related protein 1-173 isoform is selectively induced by transforming growth factor beta in articular chondrocytes and suppresses generation of extracellular inorganic pyrophosphate. Arthritis Rheum. (1998) 41:2152-64.

Truong U N et al. Parathyroid hormone related peptide (PTHrP) is a prognostic indicator in hypercalcemic cancer patients with skeletal or extra skeletal metastasis. J Bone Miner Res (1999) 14:S189.

Won C et al. Hypercalcemia in head and neck carcinoma. Incidence and prognosis. Cancer (1983) 52:2261-2263.

Yoshida A et al. Significance of the parathyroid hormone-related protein expression in breast carcinoma. Breast Cancer (2000) 7:215-20.

While preferred aspects of the present invention have been described in detail, various modifications, alterations, and changes may be made without departing from the spirit and scope of the present invention as defined in the appended claims.

SEQUENCE LISTING

```
<160> NUMBER OF SEQ ID NOS: 18

<210> SEQ ID NO 1
<211> LENGTH: 58
<212> TYPE: DNA
<213> ORGANISM: Artificial Sequence
<220> FEATURE:
<223> OTHER INFORMATION: Oligonucleotide sequence based on the sequence
      of the N-terminal region of hPTHrP amino acid residues 1 to 7

<400> SEQUENCE: 1
caccagctgt gtctgaacat cagctccttc aagagaggag ctgatgttca gacacagc        58

<210> SEQ ID NO 2
<211> LENGTH: 58
<212> TYPE: DNA
<213> ORGANISM: Artificial Sequence
<220> FEATURE:
<223> OTHER INFORMATION: Oligonucleotide sequence based on the sequence
      of the N-terminal region of hPTHrP amino acid residues 1 to 7

<400> SEQUENCE: 2
aaaagctgtg tctgaacatc agctcctctc ttgaaggagc tgatgttcag acacagct        58

<210> SEQ ID NO 3
<211> LENGTH: 7
<212> TYPE: PRT
<213> ORGANISM: Artificial Sequence
<220> FEATURE:
<223> OTHER INFORMATION: N-terminal region of hPTHrP amino acid residues
      1 to 7

<400> SEQUENCE: 3

Ala Val Ser Glu His Gln Leu
1               5

<210> SEQ ID NO 4
<211> LENGTH: 58
<212> TYPE: DNA
<213> ORGANISM: Artificial Sequence
<220> FEATURE:
```

```
<223> OTHER INFORMATION: Oligonucleotide sequence based on the sequence
      of the 3' untranslated end of hPTHrP 1-139 in exon VII

<400> SEQUENCE: 4
caccataaca ggcttctctg gcccgtattc aagagatacg ggccagagaa gcctgtta        58

<210> SEQ ID NO 5
<211> LENGTH: 58
<212> TYPE: DNA
<213> ORGANISM: Artificial Sequence
<220> FEATURE:
<223> OTHER INFORMATION: Oligonucleotide sequence based on the sequence
      of the 3' untranslated end of hPTHrP 1-139 in exon VII

<400> SEQUENCE: 5
aaaataacag gcttctctgg cccgtatctc ttgaatacgg gccagagaag cctgttat        58

<210> SEQ ID NO 6
<211> LENGTH: 27
<212> TYPE: DNA
<213> ORGANISM: Artificial Sequence
<220> FEATURE:
<223> OTHER INFORMATION: 3' untranslated end of hPTHrP 1-139 in exon VII

<400> SEQUENCE: 6
caccataaca ggcttctctg gcccgta                                          27

<210> SEQ ID NO 7
<211> LENGTH: 58
<212> TYPE: DNA
<213> ORGANISM: Artificial Sequence
<220> FEATURE:
<223> OTHER INFORMATION: Oligonucleotide sequence based on amino acids
      140-141 and the sequence of the 3' untranslated end of hPTHrP 1-
      141 in exon IX

<400> SEQUENCE: 7
caccaaggca ttgaaatttt cagcagattc aagagatctg ctgaaaattt caatgcct        58

<210> SEQ ID NO 8
<211> LENGTH: 58
<212> TYPE: DNA
<213> ORGANISM: Artificial Sequence
<220> FEATURE:
<223> OTHER INFORMATION: Oligonucleotide sequence based on amino acids
      140-141 and the sequence of the 3' untranslated end of hPTHrP 1-
      141 in exon IX

<400> SEQUENCE: 8
aaaaaggcat tgaaattttc agcagatctc ttgaatctgc tgaaaatttc aatgcctt        58

<210> SEQ ID NO 9
<211> LENGTH: 27
<212> TYPE: DNA
<213> ORGANISM: Artificial Sequence
<220> FEATURE:
<223> OTHER INFORMATION: 3' untranslated end of hPTHrP 1-141 in exon IX

<400> SEQUENCE: 9
caccaaggca ttgaaatttt cagcaga                                          27

<210> SEQ ID NO 10
<211> LENGTH: 58
<212> TYPE: DNA
<213> ORGANISM: Artificial Sequence
<220> FEATURE:
<223> OTHER INFORMATION: Oligonucleotide sequence based on the sequence
``` of the C-terminal region of hPTHrP1-173

<400> SEQUENCE: 10
caccaacagc acttctgtgg ggtttgattc aagagatcaa acccacaga agtgctgt    58

<210> SEQ ID NO 11
<211> LENGTH: 58
<212> TYPE: DNA
<213> ORGANISM: Artificial Sequence
<220> FEATURE:
<223> OTHER INFORMATION: Oligonucleotide sequence based on the sequence
      of the C-terminal region of hPTHrP1-173

<400> SEQUENCE: 11
aaaaacagca cttctgtggg gtttgatctc ttgaatcaaa ccccacagaa gtgctgtt    58

<210> SEQ ID NO 12
<211> LENGTH: 7
<212> TYPE: PRT
<213> ORGANISM: Artificial Sequence
<220> FEATURE:
<223> OTHER INFORMATION: Amino acids 140-146 of hPTHrp

<400> SEQUENCE: 12

Thr Ala Leu Leu Trp Gly Leu
1               5

<210> SEQ ID NO 13
<211> LENGTH: 25
<212> TYPE: DNA
<213> ORGANISM: Artificial Sequence
<220> FEATURE:
<223> OTHER INFORMATION: PCR Primer

<400> SEQUENCE: 13
agacgatgca gcggagactg gttca                                       25

<210> SEQ ID NO 14
<211> LENGTH: 26
<212> TYPE: DNA
<213> ORGANISM: Artificial Sequence
<220> FEATURE:
<223> OTHER INFORMATION: PCR Primer

<400> SEQUENCE: 14
ccagagaagc ctgttaccgt gaatcg                                      26

<210> SEQ ID NO 15
<211> LENGTH: 25
<212> TYPE: DNA
<213> ORGANISM: Artificial Sequence
<220> FEATURE:
<223> OTHER INFORMATION: PCR Primer

<400> SEQUENCE: 15
ggtctctgct gaaatttca atgcc                                        25

<210> SEQ ID NO 16
<211> LENGTH: 25
<212> TYPE: DNA
<213> ORGANISM: Artificial Sequence
<220> FEATURE:
<223> OTHER INFORMATION: PCR Primer

```
<400> SEQUENCE: 16
gcaggatagg tcattcactg tgctc                                              25

<210> SEQ ID NO 17
<211> LENGTH: 18
<212> TYPE: DNA
<213> ORGANISM: Artificial Sequence
<220> FEATURE:
<223> OTHER INFORMATION: PCR Primer

<400> SEQUENCE: 17
atggggaccg cccggatc                                                      18

<210> SEQ ID NO 18
<211> LENGTH: 21
<212> TYPE: DNA
<213> ORGANISM: Artificial Sequence
<220> FEATURE:
<223> OTHER INFORMATION: PCR Primer

<400> SEQUENCE: 18
tcacatgact gtctcccact c                                                  21
```

We claim:

1. A method for treating cancer in a mammal, the method comprising administering a PTHrP inhibitor to the mammal to inhibit the PTHrP1-173 isoform of PTHrP in the mammal;

wherein the inhibitor is an antibody that specifically binds with an epitope of a C-terminal portion of the human PTHrP1-173 isoform;

wherein the antibody is a monoclonal antibody produced by the hybridoma deposited with the IDAC under Accession Number 150807-01; and wherein the C-terminal portion of PTHrP1-173 (SEQ ID NO: 12) consists of amino acid residues 151-169.

2. The method of claim 1, wherein the antibody is humanized.

* * * * *